United States Patent
Kang et al.

(10) Patent No.: US 11,851,423 B2
(45) Date of Patent: *Dec. 26, 2023

(54) HETEROCYCLIC COMPOUND AND ORGANIC LIGHT EMITTING DEVICE COMPRISING THE SAME

(71) Applicant: LG CHEM, LTD., Seoul (KR)

(72) Inventors: Min Young Kang, Daejeon (KR); Tae Yoon Park, Daejeon (KR); Seongmi Cho, Daejeon (KR); Jeong Wook Mun, Daejeon (KR); Min Woo Jung, Daejeon (KR); Jung Ha Lee, Daejeon (KR)

(73) Assignee: LG Chem, Ltd., Seoul (KR)

( * ) Notice: Subject to any disclaimer, the term of this patent is extended or adjusted under 35 U.S.C. 154(b) by 280 days.

This patent is subject to a terminal disclaimer.

(21) Appl. No.: 16/603,549

(22) PCT Filed: Jul. 19, 2018

(86) PCT No.: PCT/KR2018/008155
§ 371 (c)(1),
(2) Date: Oct. 7, 2019

(87) PCT Pub. No.: WO2019/017702
PCT Pub. Date: Jan. 24, 2019

(65) Prior Publication Data
US 2020/0039971 A1 Feb. 6, 2020

(30) Foreign Application Priority Data
Jul. 19, 2017 (KR) .................. 10-2017-0091754

(51) Int. Cl.
*C07D 409/04* (2006.01)
*C07D 405/04* (2006.01)
(Continued)

(52) U.S. Cl.
CPC ......... *C07D 409/04* (2013.01); *C07D 405/04* (2013.01); *H10K 85/622* (2023.02);
(Continued)

(58) Field of Classification Search
CPC ............... C07D 409/04; C07D 405/04; C07D 409/02–06; C07D 409/10–12; C07D 409/14; C07D 405/02–06; C07D 405/10–12; C07D 405/14; C07D 307/91; C07D 333/76; C07D 493/00; C07D 495/00; H01L 51/0054; H01L 51/0067; H01L 51/0073; H01L 51/0074; H01L 51/5056; H01L 51/5072; H01L 51/5076; H01L 51/5092; H01L 51/5096; H01L 51/0062;
(Continued)

(56) References Cited

U.S. PATENT DOCUMENTS

2004/0251816 A1  12/2004  Leo et al.
2015/0249221 A1  9/2015  Zeng et al.
(Continued)

FOREIGN PATENT DOCUMENTS

CN    105315265 A    2/2016
CN    107033128 A    8/2017
(Continued)

OTHER PUBLICATIONS

English translation of WO 2016108596 A2 obtained from Global Dossier (Year: 2016).*

(Continued)

*Primary Examiner* — Dylan C Kershner
*Assistant Examiner* — Braelyn R Watson
(74) *Attorney, Agent, or Firm* — Bryan Cave Leighton Paisner LLP

(57) ABSTRACT

Provided is a heterocyclic compound Chemical Formula 1 or 2:

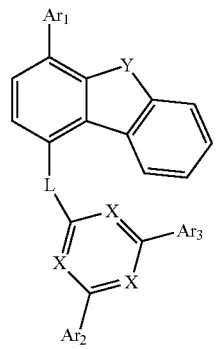

[Chemical Formula 1]

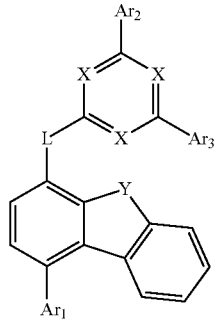

[Chemical Formula 2]

and an organic light emitting device comprising the same.

11 Claims, 1 Drawing Sheet

(51) Int. Cl.
*H10K 85/60* (2023.01)
*H10K 50/15* (2023.01)
*H10K 50/16* (2023.01)

(52) U.S. Cl.
CPC ....... *H10K 85/654* (2023.02); *H10K 85/6574* (2023.02); *H10K 85/6576* (2023.02); *H10K 50/15* (2023.02); *H10K 50/16* (2023.02)

(58) Field of Classification Search
CPC ............. H01L 51/0065; H01L 51/0068; H01L 51/0064; H01L 51/0069; H01L 51/007; H01L 51/0071; H01L 51/0072; H10K 85/622; H10K 85/654; H10K 85/6574; H10K 50/15; H10K 50/16; H10K 50/11; H10K 2101/10; H10K 85/653; H10K 85/655; H10K 85/649–6576
See application file for complete search history.

(56) References Cited

U.S. PATENT DOCUMENTS

| | | | |
|---|---|---|---|
| 2016/0028021 A1* | 1/2016 | Zeng | C07D 421/10 257/40 |
| 2016/0197285 A1 | 7/2016 | Zeng et al. | |
| 2016/0226001 A1 | 8/2016 | Parham et al. | |
| 2017/0186965 A1* | 6/2017 | Parham | H01L 51/0085 |
| 2017/0222160 A1* | 8/2017 | Lee | H05B 33/20 |
| 2018/0037546 A1 | 2/2018 | Sugino et al. | |
| 2018/0277771 A1 | 9/2018 | Park et al. | |
| 2018/0371194 A1 | 12/2018 | Abusleme et al. | |
| 2019/0363260 A1 | 11/2019 | Han et al. | |

FOREIGN PATENT DOCUMENTS

| | | | |
|---|---|---|---|
| CN | 107445910 A | 12/2017 | |
| CN | 110225909 | 9/2019 | |
| JP | 2012049518 A * | 3/2012 | |
| JP | 2017-107992 | 6/2017 | |
| KR | 10-2000-0051826 | 8/2000 | |
| KR | 10-2010-0118690 | 11/2010 | |
| KR | 10-2014-0099082 | 8/2014 | |
| KR | 10-2016-0006633 | 1/2016 | |
| KR | 10-2016-0028524 | 3/2016 | |
| KR | 10-2016-0054582 | 5/2016 | |
| KR | 10-2016-0079415 | 7/2016 | |
| KR | 10-2016-0080090 | 7/2016 | |
| KR | 10-2016-0085206 | 7/2016 | |
| KR | 10-2017-0044001 | 4/2017 | |
| KR | 10-2017-0093061 | 8/2017 | |
| KR | 10-2017-0136440 | 12/2017 | |
| KR | 10-2018-0086211 | 7/2018 | |
| KR | 10-2018-0133772 | 12/2018 | |
| WO | 2003-012890 | 2/2003 | |
| WO | WO-2007069569 A1 * | 6/2007 | ........... C07D 405/10 |
| WO | 2010/126270 | 11/2010 | |
| WO | 2016/105161 | 6/2016 | |
| WO | WO-2016108596 A2 * | 7/2016 | |
| WO | 2016-129672 | 8/2016 | |

OTHER PUBLICATIONS

English translation of WO 2007069569 A1 obtained from Global Dossier (Year: 2007).*
English translation of JP 2012049518 A obtained from Google Patents (Year: 2012).*

* cited by examiner

[FIG. 1]
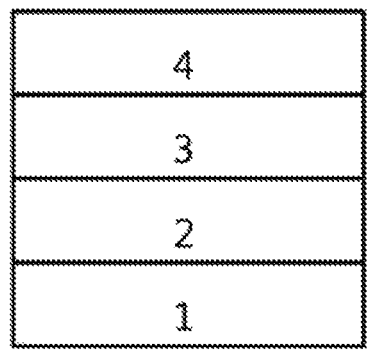
[FIG. 2]
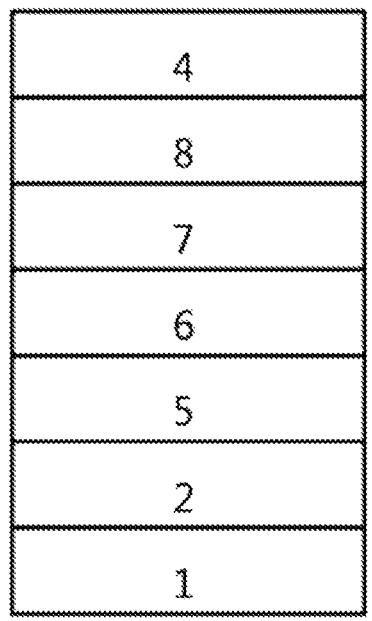

HETEROCYCLIC COMPOUND AND ORGANIC LIGHT EMITTING DEVICE COMPRISING THE SAME

CROSS-REFERENCE TO RELATED APPLICATION(S)

This application is a National Stage Application of International Application No. PCT/KR2018/008155 filed on Jul. 19, 2018, which claims the benefit of the filing date of Korean Patent Application No. 10-2017-0091754 filed with Korean Intellectual Property Office on Jul. 19, 2017, the entire content of which is incorporated herein by reference.

TECHNICAL FIELD

The present disclosure relates to a novel heterocyclic compound and to an organic light emitting device comprising the same.

Background

In general, an organic light emitting phenomenon refers to a phenomenon where electric energy is converted into light energy by using an organic material. The organic light emitting device using the organic light emitting phenomenon has characteristics such as a wide viewing angle, an excellent contrast, a fast response time, an excellent luminance, driving voltage and response speed, and thus many studies have proceeded.

The organic light emitting device generally has a structure which comprises an anode, a cathode, and an organic material layer interposed between the anode and the cathode. The organic material layer frequently has a multilayered structure that comprises different materials in order to enhance efficiency and stability of the organic light emitting device, and for example, the organic material layer can be formed of a hole injection layer, a hole transport layer, a light emitting layer, an electron transport layer, an electron injection layer and the like. In the structure of the organic light emitting device, if a voltage is applied between two electrodes, the holes are injected from an anode into the organic material layer and the electrons are injected from the cathode into the organic material layer, and when the injected holes and electrons meet each other, an exciton is formed, and light is emitted when the exciton falls to a ground state again.

There is a continuing need for the development of new materials for the organic materials used in these organic light emitting devices.

PRIOR ART LITERATURE

Patent Literature (Patent Literature 0001) Korean Patent Laid-open Publication No. 10-2000-0051826

DETAILED DESCRIPTION OF THE INVENTION

Technical Problem

It is an object of the present disclosure to provide a novel heterocyclic compound and an organic light emitting device comprising the same.

Technical Solution

According to one aspect of the present disclosure, there is provided a compound of the following Chemical Formula 1 or 2:

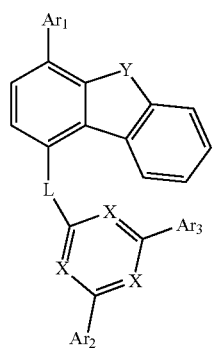

[Chemical Formula 1]

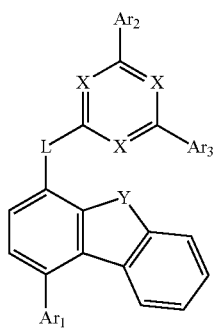

[Chemical Formula 2]

wherein in Chemical Formulas 1 and 2:
each X is independently N, or CH, provided that at least one of X is N;
Y is O or S;
L is a bond, a substituted or unsubstituted $C_{6-60}$ arylene, or a substituted or unsubstituted $C_{2-60}$ heteroarylene containing at least one hetero atom selected from the group consisting of N, O and S;
$Ar_1$ is phenyl, biphenylyl, terphenylyl, quaterphenylyl, naphthyl, phenanthrenyl, triphenylenyl, chrysenyl, fluoranthenyl, pyrenyl, or phenylenyl;
$Ar_2$ and $Ar_3$ are each independently a substituted or unsubstituted $C_{6-60}$ aryl or a substituted or unsubstituted $C_{2-60}$ heteroaryl containing at least one hetero atom selected from the group consisting of N, O and S.

According to another aspect of the present disclosure, there is provided an organic light emitting device including a first electrode; a second electrode provided opposite to the first electrode; and one or more organic material layers provided between the first electrode and the second electrode, wherein one or more layers of the organic material layers includes the compound rof Chemical Formula 1 or 2.

Advantageous Effects

The compound of Chemical Formula 1 or 2 described above can be used as a material of an organic material layer of an organic light emitting device, and can improve the efficiency, achieve low driving voltage and/or improve lifetime characteristics in the organic light emitting device. In particular, the compound of Chemical Formula 1 or 2 described above can be used as a material for hole injection, hole transport, hole injection and transport, light emitting, electron transport, or electron injection.

BRIEF DESCRIPTION OF DRAWINGS

FIG. 1 shows an example of an organic light emitting device comprising a substrate 1, an anode 2, a light emitting layer 3, and a cathode 4.

FIG. 2 shows an example of an organic light emitting device comprising a substrate 1, an anode 2, a hole injection layer 5, a hole transport layer 6, a light emitting layer 7, an electron transport layer 8, and a cathode 4.

DETAILED DESCRIPTION OF THE EMBODIMENTS

Hereinafter, the present invention will be described in more detail to help understanding of the present invention.

In one embodiment of the present disclosure, there is provided a compound of Chemical Formula 1 or 2.

As used herein, the notation,  or  means a bond linked to another substituent group.

As used herein, the term "substituted or unsubstituted" means being unsubstituted or substituted with one or more substituents selected from the group consisting of deuterium, a halogen group, a nitrile group, a nitro group, a hydroxy group, a carbonyl group, an ester group, an imide group, an amino group, a phosphine oxide group, an alkoxy group, an aryloxy group, an alkylthioxy group, an arylthioxy group, an alkylsulfoxy group, an arylsulfoxy group, a silyl group, a boron group, an alkyl group, a cycloalkyl group, an alkenyl group, an aryl group, an aralkyl group, an aralkenyl group, an alkylaryl group, an alkylamine group, an aralkylamine group, a heteroarylamine group, an arylamine group, an arylphosphine group, and a hetero-cyclic group containing at least one of N, O and S atoms, or being unsubstituted or substituted with a substituent to which two or more substituents are linked among the substituents exemplified above. For example, "the substituent to which two or more substituents are linked" can be a biphenyl group. That is, the biphenyl group can also be an aryl group, and can be interpreted as a substituent to which two phenyl groups are linked.

In the present disclosure, the number of carbon atoms of a carbonyl group is not particularly limited, but is preferably 1 to 40. Specifically, the carbonyl group can be a compound having the following structural formulae, but is not limited thereto:

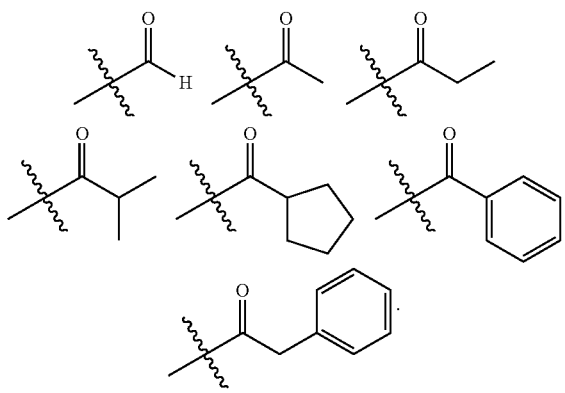

In the present disclosure, for an ester group, the oxygen of the ester group can be substituted with a straight-chain, branched-chain, or cyclic alkyl group having 1 to 25 carbon atoms, or an aryl group having 6 to 25 carbon atoms. Specifically, the ester group can be a compound having the following structural formulae, but is not limited thereto:

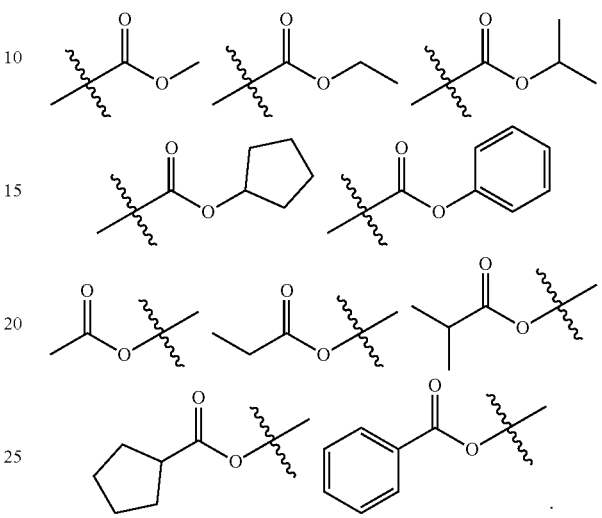

In the present disclosure, the number of carbon atoms of an imide group is not particularly limited, but is preferably 1 to 25. Specifically, the imide group can be a compound having the following structural formulae, but is not limited thereto:

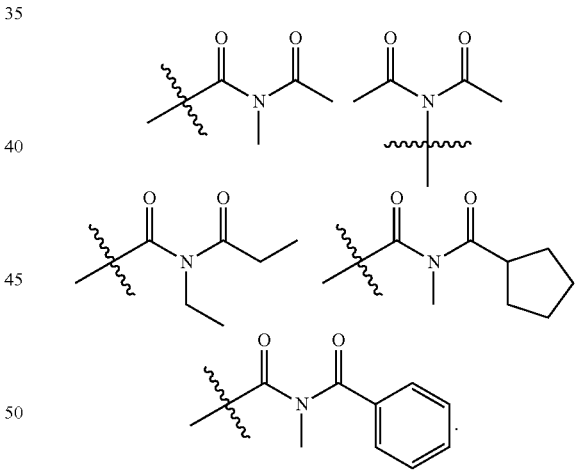

In the present disclosure, the silyl group specifically includes a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but is not limited thereto.

In the present disclosure, the boron group specifically includes a trimethylboron group, a triethylboron group, a t-butyldimethylboron group, a triphenylboron group, and a phenylboron group, but is not limited thereto.

In the present disclosure, examples of a halogen group include fluorine, chlorine, bromine, or iodine.

In the present disclosure, the alkyl group can be a straight chain or branched chain, and the number of carbon atoms thereof is not particularly limited, but is preferably 1 to 40. According to one embodiment, the number of carbon atoms of the alkyl group is 1 to 20. According to another embodiment, the number of carbon atoms of the alkyl group is 1 to 10. According to another embodiment, the number of carbon atoms of the alkyl group is 1 to 6, Specific examples of the alkyl group include methyl, ethyl, propyl, n-propyl, isopropyl, butyl, n-butyl, isobutyl, tert-butyl, sec-butyl, 1-methylbutyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethylpropyl, 1,1-dimethyl-propyl, isohexyl, 2-methylpentyl, 4-methylhexyl, 5-methylhexyl, and the like, but are not limited thereto.

In the present disclosure, the alkenyl group can be a straight chain or branched chain, and the number of carbon atoms thereof is not particularly limited, but is preferably 2 to 40. According to one embodiment, the number of carbon atoms of the alkenyl group is 2 to 20. According to another embodiment, the number of carbon atoms of the alkenyl group is 2 to 10. According to still another embodiment, the number of carbon atoms of the alkenyl group is 2 to 6. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present disclosure, a cycloalkyl group is not particularly limited, but the number of carbon atoms thereof is preferably 3 to 60. According to one embodiment, the number of carbon atoms of the cycloalkyl group is 3 to 30. According to another embodiment, the number of carbon atoms of the cycloalkyl group is 3 to 20. According to still another embodiment, the number of carbon atoms of the cycloalkyl group is 3 to 6. Specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-di methylcyclohexyl, 3,4,5-trimethylcyclohexyl, 4-tert-butylcyclohexyl, cycloheptyl, cyclooctyl, and the like, but are not limited thereto.

In the present disclosure, the aryl group is not particularly limited, but preferably has 6 to 60 carbon atoms, and can be a monocyclic aryl group or a polycyclic aryl group. According to one embodiment, the number of carbon atoms of the aryl group is 6 to 30. According to one embodiment, the number of carbon atoms of the aryl group is 6 to 20. The aryl group can be a phenyl group, a biphenyl group, a terphenyl group or the like as the monocyclic aryl group, but is not limited thereto. Examples of the polycyclic aryl group include a naphthyl group, an anthracenyl group, a phenanthryl group, a pyrenyl group, a perylenyl group, a chrysenyl group and a fluorenyl group or the like, but is not limited thereto.

In the present disclosure, a fluorenyl group can be substituted, and two substituent groups can be bonded to each other to form a spiro structure. In the case where the fluorenyl group is substituted,

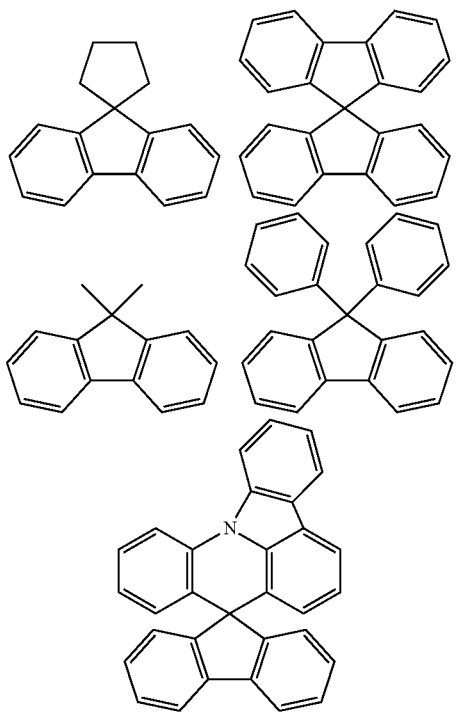

and the like can be formed. However, the structure is not limited thereto.

In the present disclosure, the heterocyclic group is a heterocyclic group including one or more of O, N, Si and S as a heteroatom, and the number of carbon atoms thereof is not particularly limited, but is preferably 2 to 60. Examples of the heterocyclic group include a thiophene group, a furan group, a pyrrole group, an imidazole group, a thiazole group, an oxazol group, an oxadiazol group, a triazol group, a pyridyl group, a bipyridyl group, a pyrimidyl group, a triazine group, an acridyl group, a pyridazine group, a pyrazinyl group, a quinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzimidazole group, a benzothiazol group, a benzocarbazole group, a benzothiophene group, a dibenzothiophene group, a benzofuranyl group, a phenanthroline group, an isoxazolyl group, a thiadiazolyl group, a phenothiazinyl group, a dibenzofuranyl group, and the like, but are not limited thereto.

In the present disclosure, the aryl group in the aralkyl group, the aralkenyl group, the alkylaryl group, and the arylamine group is the same as the aforementioned examples of the aryl group. In the present disclosure, the alkyl group in the aralkyl group, the alkylaryl group and the alkylamine group is the same as the aforementioned examples of the alkyl group. In the present disclosure, the heteroaryl in the heteroarylamine can be applied to the aforementioned description of the heterocyclic group. In the present disclosure, the alkenyl group in the aralkenyl group is the same as the aforementioned examples of the alkenyl group. In the present disclosure, the aforementioned description of the aryl group can be applied except that the arylene is a divalent group. In the present disclosure, the aforementioned description of the heterocyclic group can be applied except that the heteroarylene is a divalent group. In the present disclosure, the aforementioned description of the aryl group or cycloalkyl group can be applied except that the hydrocarbon ring is not a monovalent group but formed by combining two substituent groups. In the present disclosure, the aforementioned description of the heterocyclic group can be applied, except that the heterocycle is not a monovalent group but formed by combining two substituent groups.

In Chemical=formulas Formulas 1 and 2, L is preferably a bond, phenylene, biphenyldiyl, or terphenyldiyl.

Preferably, Ar and Ar are each independently phenyl, biphenylyl, dibenzofuranyl, or dibenzothiophenyl.

Preferably, Ar is phenyl, and Ar is phenyl, biphenylyl, dibenzofuranyl, or dibenzothiophenyl.

Representative examples of the compound of Chemical Formula 1 or 2 are as follows:

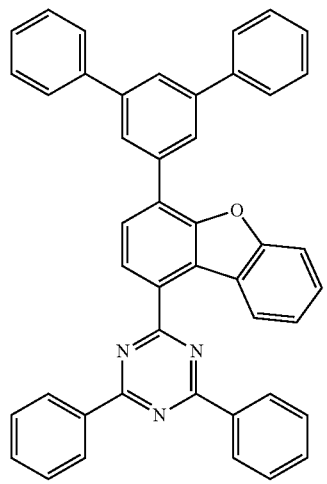

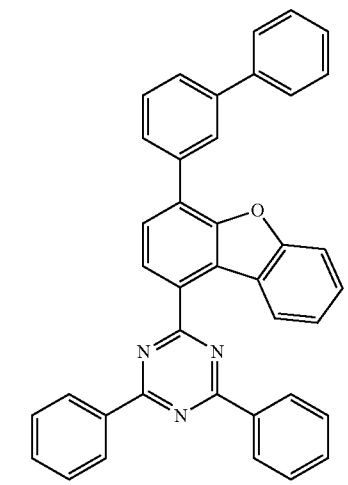

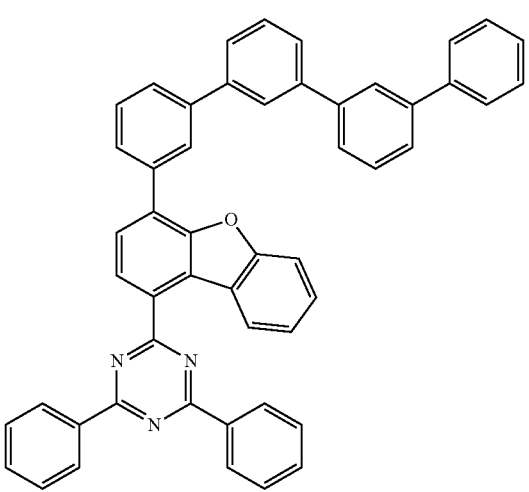

-continued

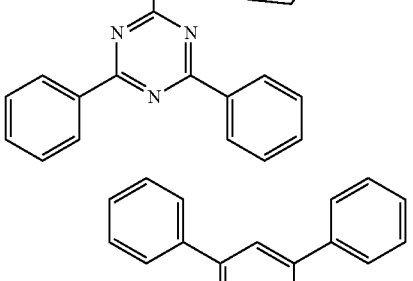

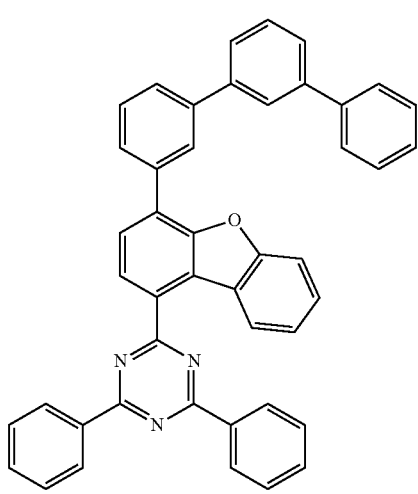

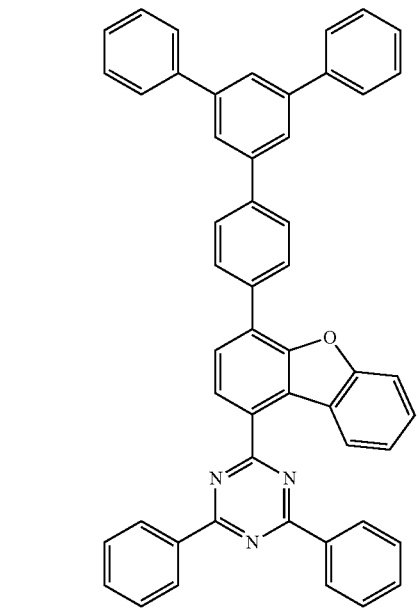

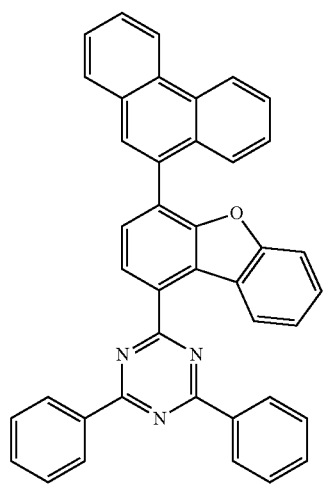
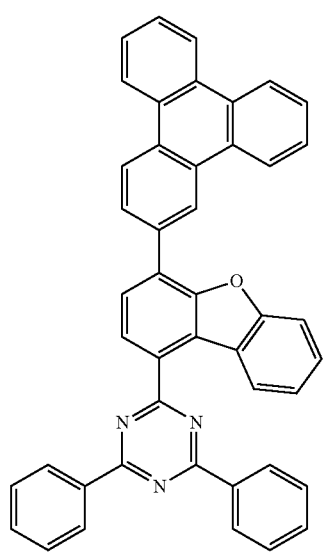
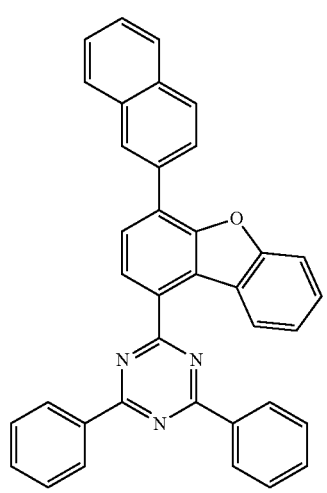
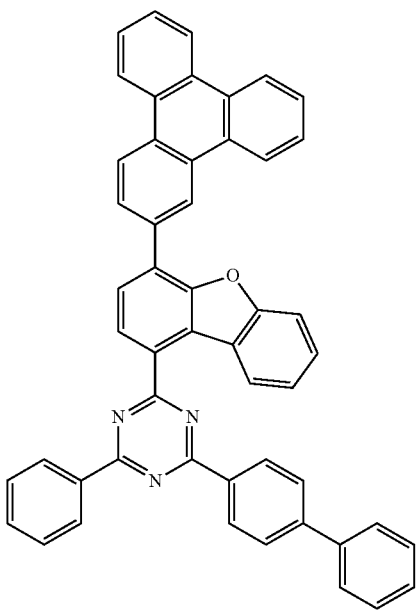
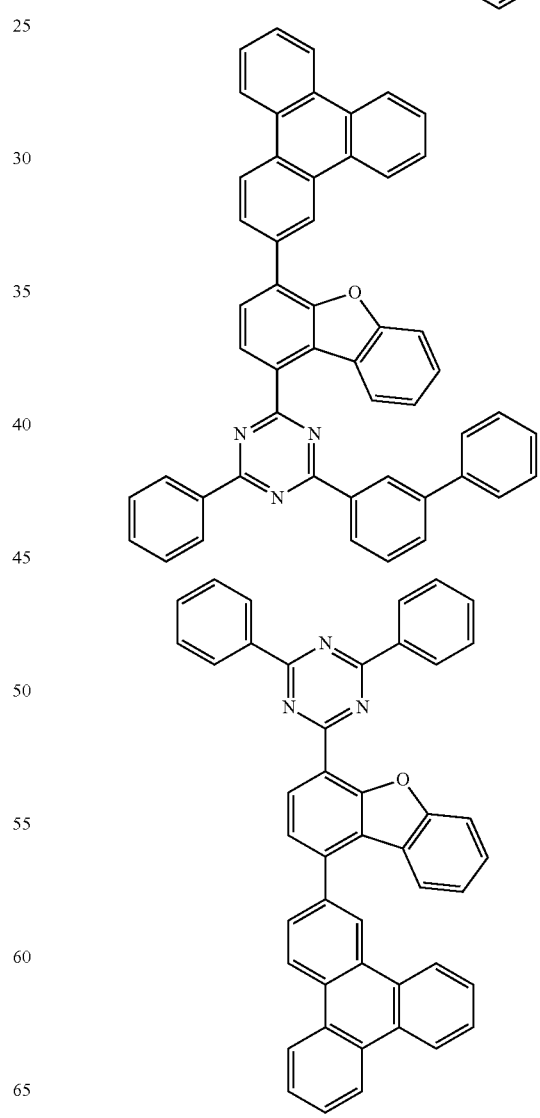

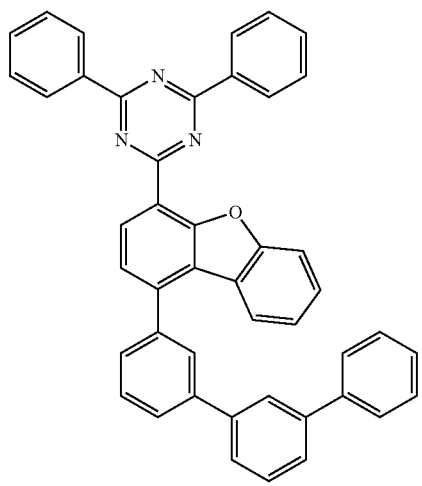
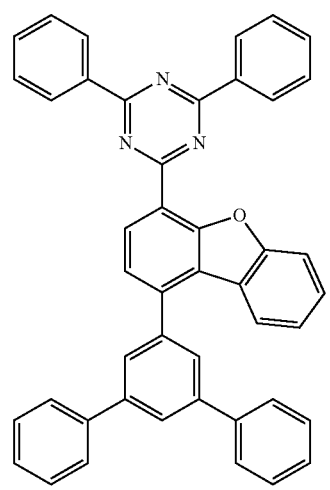
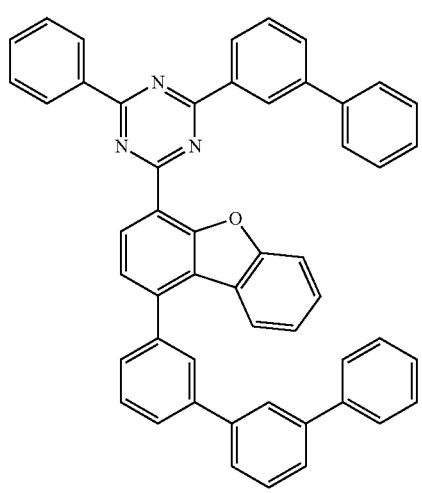
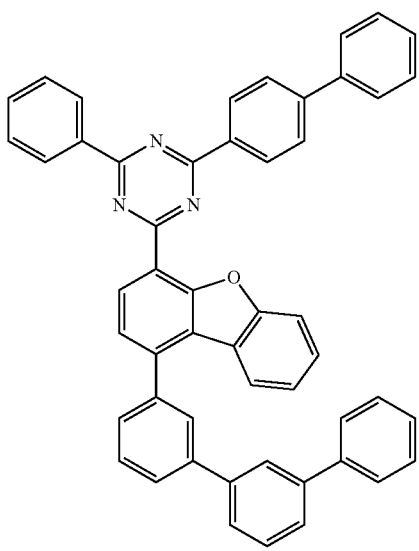 [SMILES: c1ccc(-c2ccc(-c3nc(-c4ccccc4)nc(-c4ccc(-c5cccc(-c6cccc(-c7ccccc7)c6)c5)c5c4sc4ccccc45)n3)cc2)cc1]
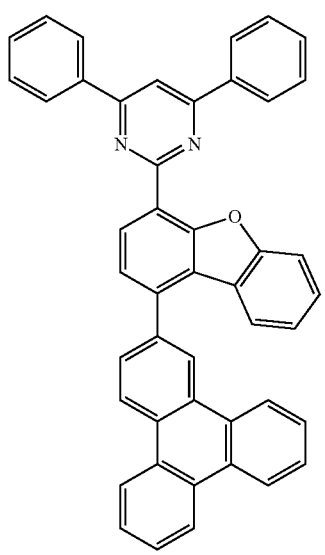
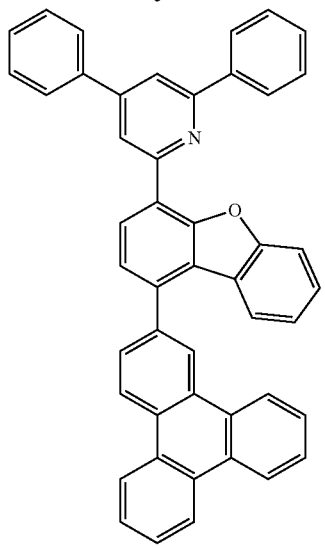

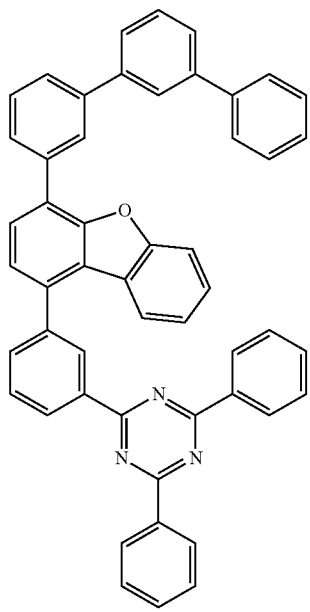
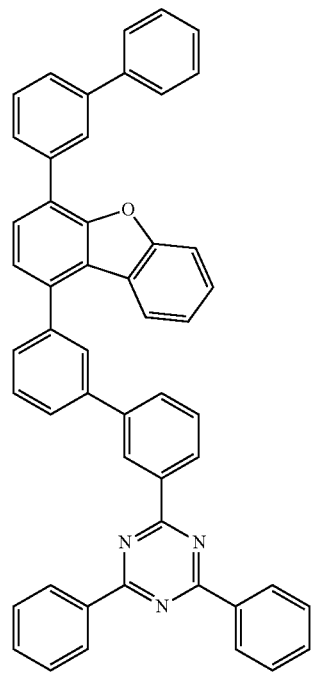
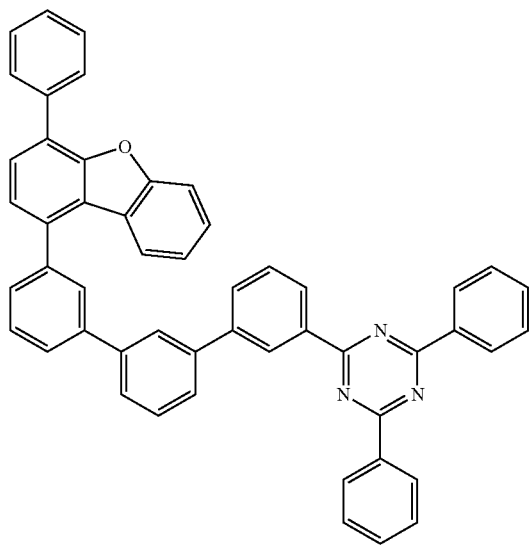
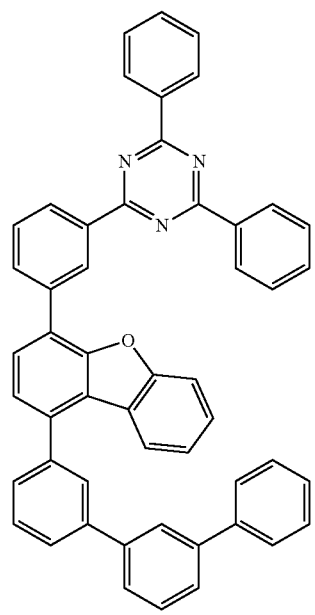

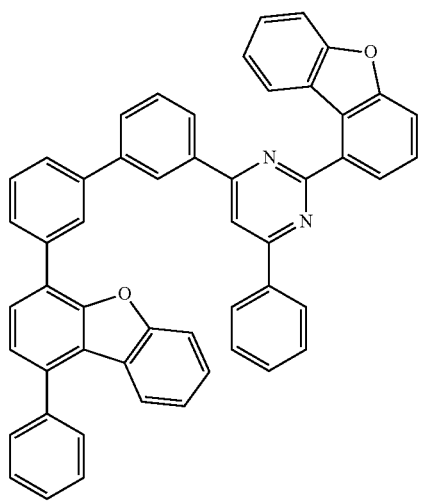
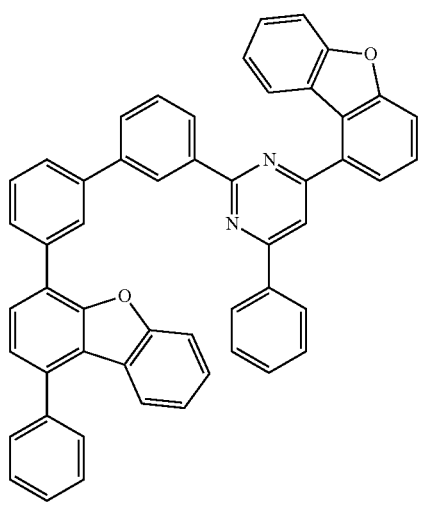
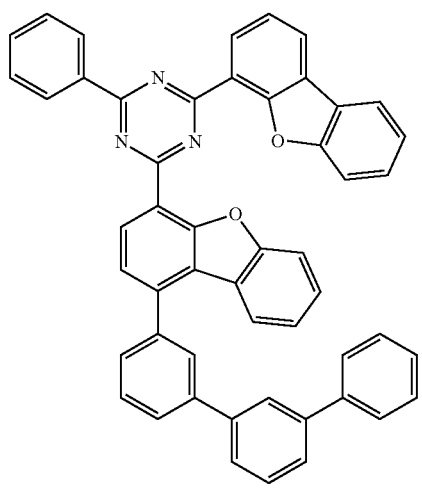
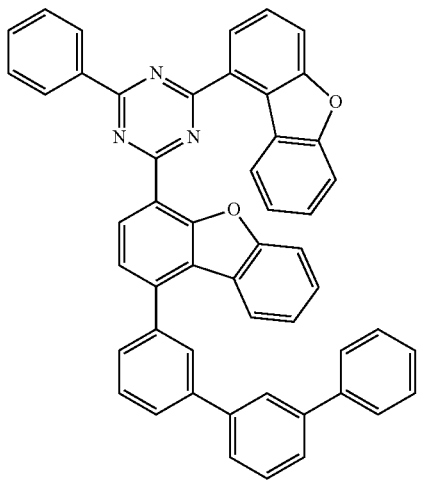
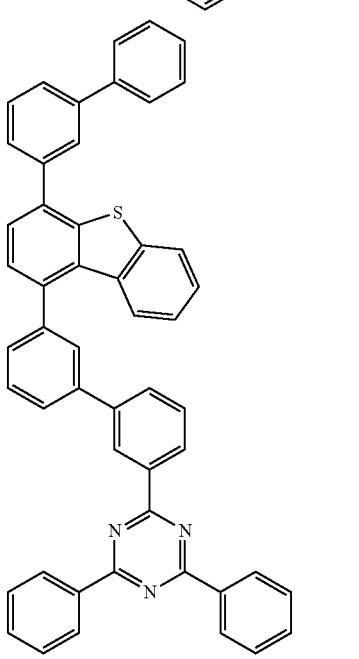
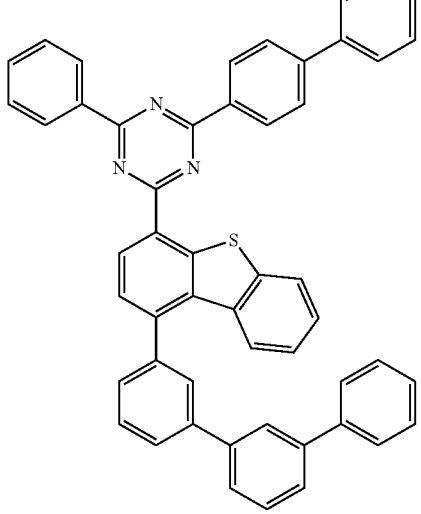

The compound of Chemical Formula 1 or 2 can be respectively prepared by the preparation method as shown in the following Reaction Scheme 1 or 2.

[Reaction Scheme 1]

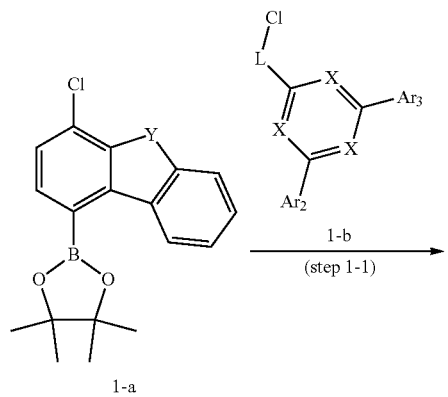

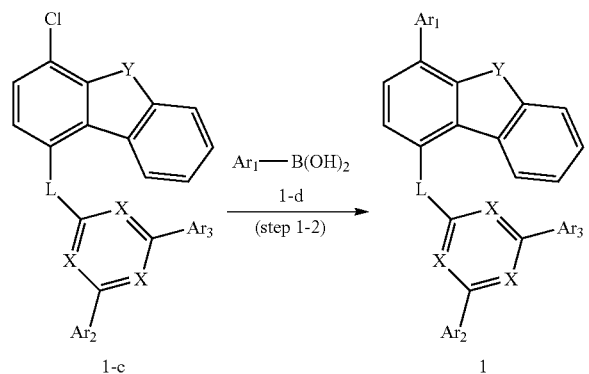

[Reaction Scheme 2]

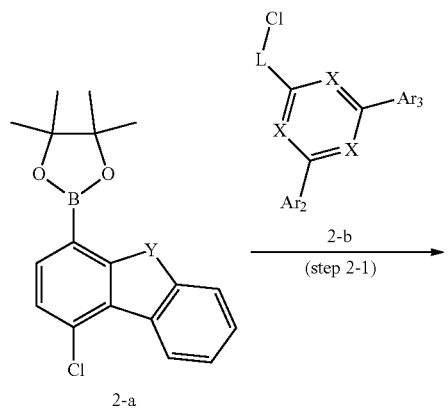

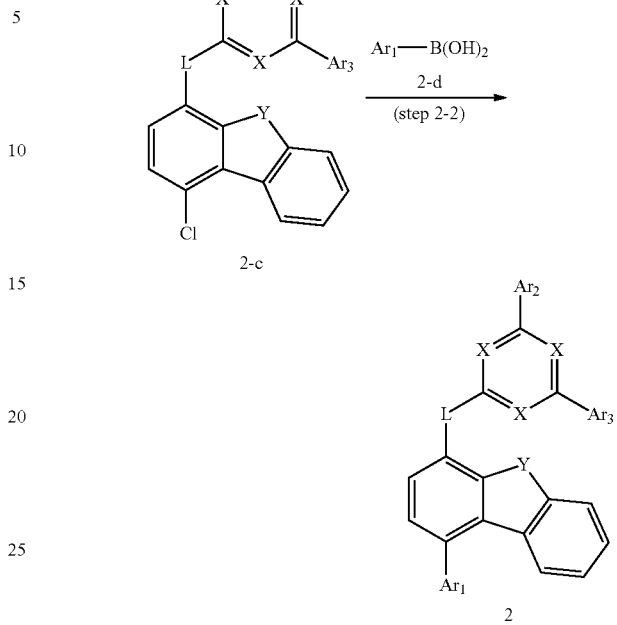

Each step of the Reaction Schemes 1 and 2 is a Suzuki coupling reaction, which is preferably carried out in the presence of a palladium catalyst and a base, and the reactive group for the Suzuki coupling reaction can be modified as known in the art. The above preparation method can be further specified in Preparation Examples to be described later.

According to another embodiment of the present disclosure, there is provided an organic light emitting device including a compound of Chemical Formula 1 or 2. As an example, the present disclosure provides an organic light emitting device including: a first electrode; a second electrode provided opposite to the first electrode; and one or more organic material layers provided between the first electrode and the second electrode, wherein one or more layers of the organic material layers includes the compound of Chemical Formula 1 or 2.

The organic material layer of the organic light emitting device of the present disclosure can have a single layer structure, or it can have a multilayered structure in which two or more organic material layers are stacked. For example, the organic light emitting device of the present disclosure can have a structure comprising a hole injection layer, a hole transport layer, a light emitting layer, an electron transport layer, an electron injection layer and the like as the organic material layer. However, the structure of the organic light emitting device is not limited thereto, and it can include a smaller number of organic layers.

Further, the organic material layer can include a hole injection layer, a hole transport layer, or a layer simultaneously performing hole injection and transport, wherein the hole injection layer, the hole transport layer, and the layer simultaneously performing hole injection and transport include a compound of Chemical Formula 1 or 2.

Further, the organic material layer can include a light emitting layer, wherein the light emitting layer can include a compound of Chemical formula Formula 1 or 2.

Further, the organic material layer can include an electron transport layer, or an electron injection layer, wherein the electron transport layer, or the electron injection layer includes a compound of Chemical Formula 1 or 2, Further, the electron transport layer, the electron injection layer, or a layer simultaneously performing electron transport and electron injection include a compound of Chemical Formula 1 or 2.

Further, the organic material layer includes a light emitting layer and an electron transport layer, wherein the electron transport layer can include a compound of Chemical Formula 1 or 2.

Further, the organic light emitting device according to the present disclosure can be a normal type organic light emitting device in which an anode, one or more organic material layers, and a cathode are sequentially stacked on a substrate. Further, the organic light emitting device according to the present disclosure can be an inverted type organic light emitting device in which a cathode, one or more organic material layers and an anode are sequentially stacked on a substrate. For example, the structure of an organic light emitting device according to an embodiment of the present disclosure is illustrated in FIGS. 1 and 2.

FIG. 1 shows an example of an organic light emitting device comprising a substrate 1, an anode 2, a light emitting layer 3, and a cathode 4. In such a structure, the compound of Chemical Formula 1 or 2 can be included in the light emitting layer.

FIG. 2 shows an example of an organic light emitting device including a substrate 1, an anode 2, a hole injection layer 5, a hole transport layer 6, a light emitting layer 7, an electron transport layer 8, and a cathode 4. In such a structure, the compound of the Chemical Formula 1 or the Chemical Formula 2 can be included in one or more layers of the hole injection layer, the hole transport layer, and the electron transport layer.

The organic light emitting device according to the present disclosure can be manufactured by materials and methods known in the art, except that one or more layers of the organic material layers includes the compound of Chemical Formula 1 or 2. In addition, when the organic light emitting device includes a plurality of organic material layers, the organic material layers can be formed of the same material or different materials.

For example, the organic light emitting device according to the present disclosure can be manufactured by sequentially stacking a first electrode, an organic material layer and a second electrode on a substrate. In this case, the organic light emitting device can be manufactured by depositing a metal, metal oxides having conductivity, or an alloy thereof on the substrate using a PVD (physical vapor deposition) method such as a sputtering method or an e-beam evaporation method to form an anode, forming organic material layers including the hole injection layer, the hole transport layer, the light emitting layer, and the electron transport layer thereon, and then depositing a material that can be used as the cathode thereon. In addition to such a method, the organic light emitting device can be manufactured by sequentially depositing a cathode material, an organic material layer and an anode material on a substrate.

In addition, the compound of Chemical Formula 1 or 2 can be formed into an organic layer by a solution coating method as well as a vacuum deposition method at the time of manufacturing an organic light emitting device. Herein, the solution coating method means a spin coating, a dip coating, a doctor blading, an inkjet printing, a screen printing, a spray method, a roll coating, or the like, but is not limited thereto.

In addition to such a method, the organic light emitting device can be manufactured by sequentially depositing a cathode material, an organic material layer and an anode material on a substrate (International Publication WO20031012890). However, the manufacturing method is not limited thereto.

As an example, the first electrode is an anode, and the second electrode is a cathode, or alternatively the first electrode is a cathode and the second electrode is an anode.

As the anode material, generally, a material having a large work function is preferably used so that holes can be smoothly injected into the organic material layer. Specific examples of the anode material include metals such as vanadium, chrome, copper, zinc, and gold, or an alloy thereof; metal oxides such as zinc oxides, indium oxides, indium tin oxides (ITO), and indium zinc oxides (IZO); a combination of metals and oxides, such as ZnO:Al or SNO:Sb; conductive polymers such as poly(3-methylthiophene), poly[3,4-(ethylene-1,2-dioxy)-thiophene] (PEDOT), polypyrrole, and polyaniline, and the like, but are not limited thereto.

As the cathode material, generally, a material having a small work function is preferably used so that electrons can be easily injected into the organic material layer. Specific examples of the cathode material include metals such as magnesium, calcium, sodium, potassium, titanium, indium, yttrium, lithium, gadolinium, aluminum, silver, tin, and lead, or an alloy thereof; a multilayered structure material such as LiF/Al or LiO/Al, and the like, but are not limited thereto.

The hole injection layer is a layer for injecting holes from the electrode, and the hole injection material is preferably a compound which has a capability of transporting the holes, thus has a hole injecting effect in the anode and an excellent hole injecting effect to the light emitting layer or the light emitting material, prevents excitons produced in the light emitting layer from moving to a hole injection layer or the electron injection material, and is excellent in the ability to form a thin film. It is preferable that a HOMO (highest occupied molecular orbital) of the hole injection material is between the work function of the anode material and a HOMO of a peripheral organic material layer. Specific examples of the hole injection material include metal porphyrine, oligothiophene, an arylamine-based organic material, a hexanitrilehexaazatriphenylene-based organic material, a quinacridone-based organic material, a perylene-based organic material, anthraquinone, polyaniline and polythiophene-based conductive polymer, and the like, but are not limited thereto.

The hole transport layer is a layer that receives holes from hole injection layer and transports the holes to the light emitting layer. The hole transport material is suitably a material having large mobility to the holes, which can receive holes from the anode or the hole injection layer and transfer the holes to the light emitting layer. Specific examples thereof include an arylamine-based organic material, a conductive polymer, a block copolymer in which a conjugate portion and a non-conjugate portion are present together, and the like, but are not limited thereto.

The light emitting material is preferably a material which can receive holes and electrons transported from a hole transport layer and an electron transport layer, respectively, and combine the holes and the electrons to emit light in a visible ray region, and has good quantum efficiency to fluorescence or phosphorescence. Specific examples of the light emitting material include an 8-hydroxy-quinoline aluminum complex (Alq); a carbazole-based compound; a dimerized styryl compound; BAlq; a 10-hydroxybenzoquinoline-metal compound; a benzoxazole, benzthiazole and benzimidazole-based compound; a poly(p-phenylenevinylene) (PPV)-based polymer; a spiro compound; polyfluorene, lubrene, and the like, but are not limited thereto.

The light emitting layer can include a host material and a dopant material. The host material can be a fused aromatic ring derivative, a heterocycle-containing compound or the like. Specific examples of the fused aromatic ring derivatives include anthracene derivatives, pyrene derivatives, naphthalene derivatives, pentacene derivatives, phenanthrene compounds, fluoranthene compounds, and the like. Examples of the heterocyclic-containing compounds include carbazole derivatives, dibenzofuran derivatives, ladder-type furan compounds, pyrimidine derivatives, and the like, but are not limited thereto.

Examples of the dopant material include an aromatic amine derivative, a styrylamine compound, a boron complex, a fluoranthene compound, a metal complex, and the like. Specifically, the aromatic amine derivative is a substituted or unsubstituted fused aromatic ring derivative having an arylamino group, and examples thereof include pyrene, anthracene, chrysene, periflanthene and the like, which have an arylamino group. The styrylamine compound is a compound where at least one arylvinyl group is substituted in substituted or unsubstituted arylamine, in which one or two or more substituent groups selected from the group consisting of an aryl group, a silyl group, an alkyl group, a cycloalkyl group, and an arylamino group are substituted or unsubstituted. Specific examples thereof include styrylamine, styryldiamine, styryltriamine, styryltetramine, and the like, but are not limited thereto. Further, the metal complex includes an iridium complex, a platinum complex, and the like, but is not limited thereto.

The electron transport layer is a layer which receives electrons from an electron injection layer and transports the electrons to a light emitting layer, and an electron transport material is suitably a material which can receive electrons well from a and transfer the electrons to a light emitting layer, and has a large mobility for electrons. Specific examples of the electron transport material include: an Al complex of 8-hydroxyquinoline; a complex including Alq; an organic radical compound; a hydroxyflavone-metal complex, and the like, but are not limited thereto. The electron transport layer can be used with any desired cathode material, as used according to the related art. In particular, appropriate examples of the cathode material are a typical material which has a low work function, followed by an aluminum layer or a silver layer. Specific examples thereof include cesium, barium, calcium, ytterbium, and samarium, in each case followed by an aluminum layer or a silver layer.

The electron injection layer is a layer which injects electrons from an electrode, and is preferably a compound which has a capability of transporting electrons, has an effect of injecting electrons from a cathode and an excellent effect of injecting electrons into a light emitting layer or a light emitting material, prevents excitons produced from the light emitting layer from moving to a hole injection layer, and is also excellent in the ability to form a thin film. Specific examples of the electron injection layer include fluorenone, anthraquinodimethane, diphenoquinone, thiopyran dioxide, oxazole, oxadiazole, triazole, imidazole, perylenetetracarboxylic acid, fluorenylidene methane, anthrone, and the like, and derivatives thereof, a metal complex compound, a nitrogen-containing 5-membered ring derivative, and the like, but are not limited thereto.

Examples of the metal complex compound include 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato)gallium, bis(10-hydroxy-benzo[h]quinolinato)beryllium, bis(10-hydroxybenzo[h]quinolinato)zinc, bis(2-methyl-8-quinolinato)chlorogallium, bis(2-methyl-8-quinolinato)(o-cresolato)-gallium, bis(2-methyl-8-quinolinato)(1-naphtholato)aluminum, bis(2-methyl-8-quinolinato)(2-naphtholato)gallium, and the like, but are not limited thereto.

The organic light emitting device according to the present disclosure can be a front side emission type, a back side emission type, or a double side emission type according to the used material.

In addition, the compound of Chemical Formula 1 or 2 can be included in an organic solar cell or an organic transistor in addition to an organic light emitting device.

The preparation of the compound of Chemical Formula 1 or 2 and the organic light emitting device comprising the same will be described in detail in the following examples. However, these examples are presented for illustrative purposes only, and the scope of the present invention is not limited thereto.

PREPARATION EXAMPLE

Preparation Example 1: Preparation of Compound A

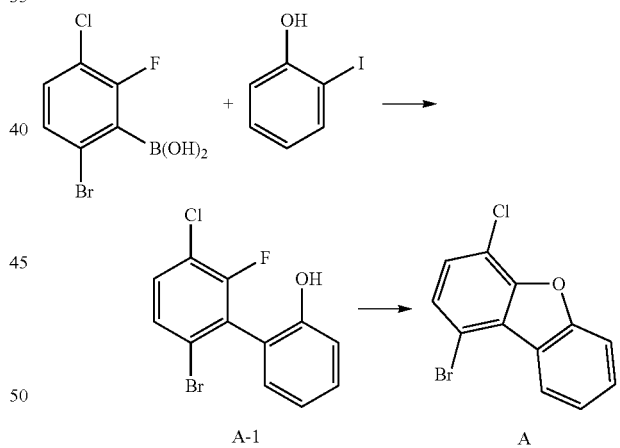

Step 1) Preparation of Compound A-1

After (6-bromo-3-chloro-2-fluorophenyl)boronic acid (25 g, 98.7 mmol) and 2-iodophenol (21.7 g, 98.7 mmol) were dispersed in tetrahydrofuran (250 mL), 2M aqueous potassium carbonate solution (eq. K) (98 mL, 197.4 mmol) was added and tetrakistriphenylphosphinopalladium [Pd(PPh] (1.1 mg, 1 mol %) was added thereto, and then the mixture was stirred under reflux for 6 hours. The temperature was lowered to room temperature, the aqueous layer was separated and the organic layer was further washed once more with water to separate the organic layer. The collected organic layer was slurried with anhydrous magnesium sulfate, filtered and concentrated under reduced pressure. The compound in the form of oil was separated by silica chromatography using a combination of hexane and ethyl acetate to produce Compound A-1 (19.3 g, yield: 65%).

Step 2) Preparation of Compound A

Compound A-1 (20 g, 66.3 mmol) was diluted in 100 mL of N-methyl-2-pyrrolidone, and potassium carbonate (13.7 g, 99.5 mmol) was added thereto and heated to 140° C. After about 1 hour, the reaction was cooled to room temperature and slowly added to 1 L of water. The precipitated solid was filtered, which was then dissolved in tetrahydrofuran, treated with anhydrous magnesium sulfate and filtered. The filtrate was then concentrated under reduced pressure. The concentrated compound was slurried with a small amount of tetrahydrofuran and an excess amount of hexane and filtered. To purify the filtered compound, it was separated by silica chromatography with hexane and ethyl acetate to produce Compound A (13.6 g, yield: 73%).

Example 1

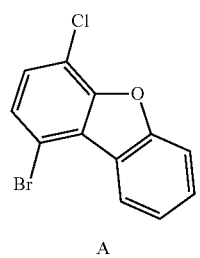

A

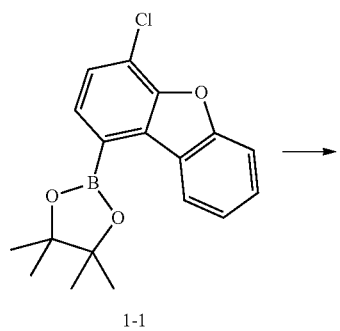

1-1

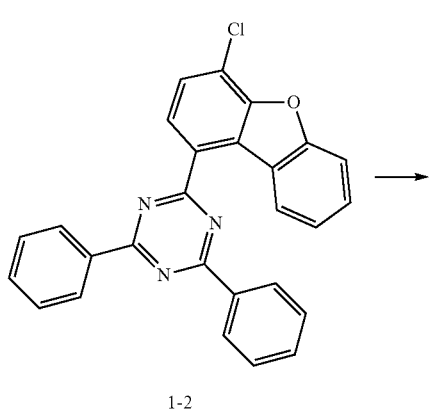

1-2

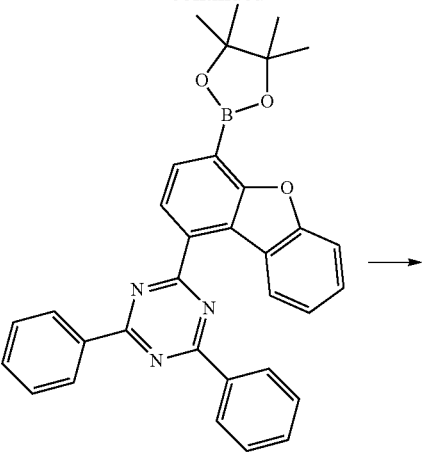

1-3

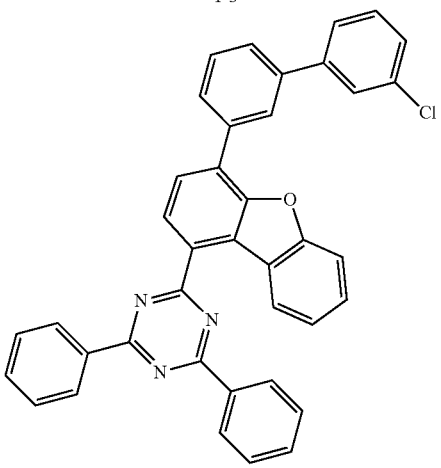

1-4

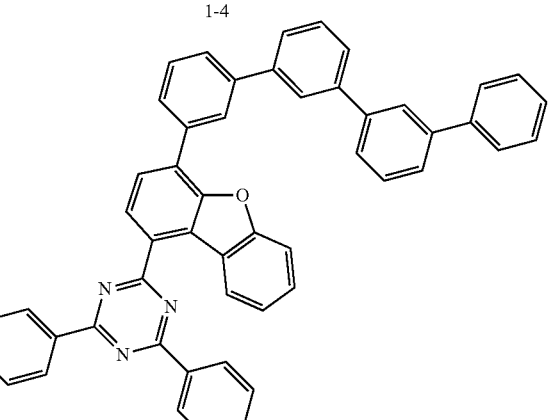

1

Step 1) Preparation of Compound 1-1

Compound A (30 g, 107 mmol), bis(pinacolato)diborone (36.6 g, 127.9 mmol), and potassium acetate (20.9 g, 213 mmol) were added to 300 mL of 1,4-dioxane. Dibenzylidene acetone palladium (1.8 g, 3.2 mmol) and tricyclohexylphosphine (1.8 g, 6.4 mmol) were added thereto under refluxing and stirring conditions, and the resulting mixture was refluxed and stirred for 12 hours. When the reaction was completed, the reaction mixture was cooled to room temperature and filtered through celite. The filtrate was concentrated under reduced pressure, and the residue was dissolved in chloroform and washed with water to separate an organic layer, which was then dried over anhydrous magnesium sulfate. The resultant was filtered, distilled under reduced pressure, and stirred with ethyl acetate and ethanol to produce Compound 1-1 (30.1 g, yield: 86%).

Step 2) Preparation of Compound 1-2

After Compound A (25 g, 76 mmol) and 2-chloro-4,6-diphenyl-1,3,5-triazine (20.3 g, 76 mmol) were dispersed in 200 mL of tetrahydrofuran, 2M aqueous potassium carbonate solution (aq. K) (57 mL, 114 mmol) was added and tetrakistriphenylphosphinopalladium [Pd(PPh] (0.88 g, 1 mol %) was added thereto, and then mixture was stirred under reflux for 6 hours. The temperature was lowered to room temperature, the aqueous layer was separated and the organic layer was concentrated under reduced pressure. The concentrated compound was re-dissolved in ethyl acetate and then washed twice with water, separated, treated with anhydrous magnesium sulfate, filtered and concentrated. To the concentrated residue was added a small amount of ethyl acetate and an excess amount of hexane, and the mixture was stirred to precipitate a solid, which was stirred for 1 hour and then filtered to produce the desired Compound 1-2 (26.7 g, yield: 81%).

Step 3) Preparation of Compound 1-3

Compound 1-3 (24.2 g, yield: 80%) was prepared in the same manner as in Step 1 of Example 1 by using Compound 1-2 (25 g, 58 mmol).

Step 4) Preparation of Compound 1-4

Compound 1-4 (16.2 g, yield: 73%) was prepared in the same manner as in Step 2 of Example 1 by using Compound 1-3 (20 g, 38 mmol) and 3-bromo-3'-chloro-1,1'-biphenyl (10.2 g, 38 mmol).

Step 5) Preparation of Compound 1

Compound 1-4 (20 g, 34 mmol) and [1,1'-biphenyl]-3-ylboronic acid (7.4 g, 38 mmol) were added to 1,4-dioxane (150 mL), and potassium phosphate (14.5 g, 68 mmol) and water (50 mL) were further added thereto. Dibenzylidene acetone palladium (0.6 g, 1 mol %) and tricyclohexylphosphine (0.6 g, 1 mol %) were added under refluxing and stirring conditions, and the resulting mixture was refluxed and stirred for 12 hours. When the reaction was completed, the reaction mixture is cooled to room temperature to separate an aqueous layer, which was concentrated under reduced pressure. The residue was then dissolved in chloroform and washed with water to separate an organic layer. The separated organic layer was dried over anhydrous magnesium sulfate and filtered. The filtrate was concentrated under reduced pressure and purified by silica column chromatography with hexane and chloroform to produce Compound 1-4 (16.2 g, yield: 73%).

MS: [M+H]=704

Example 2

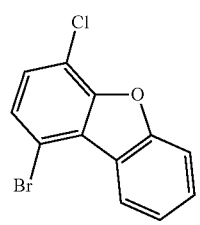

A

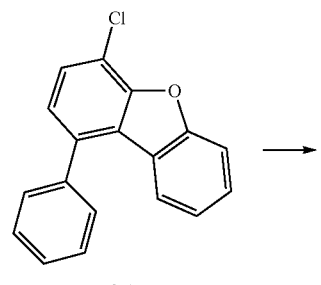

2-1

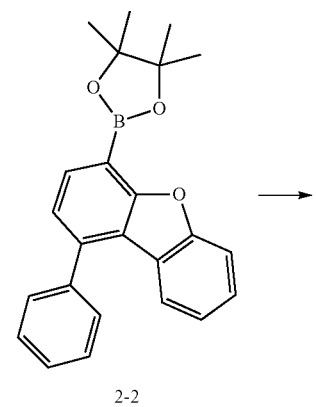

2-2

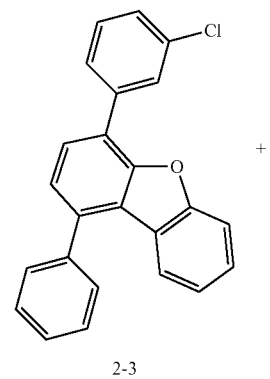

2-3

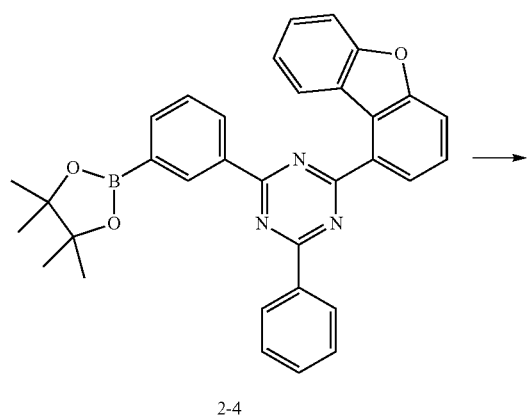

2-4

27
-continued

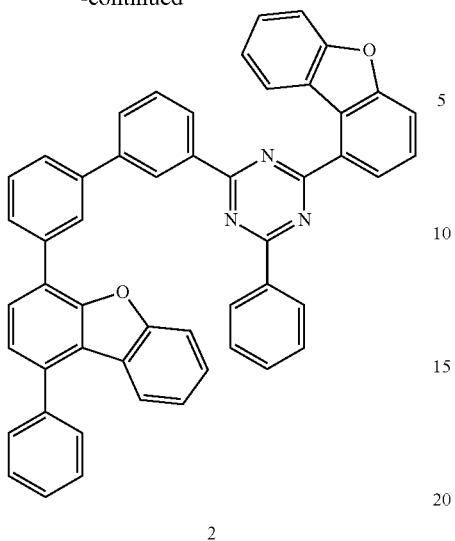

2

Step 1) Preparation of Compound 2-1

Compound 2-1 (20.5 g, yield: 83%) was prepared in the same manner as in Step 2 of Example 1 by using Compound A (25 g, 88.8 mmol) and phenylboronic acid (11.9 g, 97.7 mmol).

Step 2) Preparation of Compound 2-2

Compound 2-2 (28.6 g, yield: 86%) was prepared in the same manner as in Step 1 of Example 1 by using Compound 2-1 (25 g, 89.7 mmol).

Step 3) Preparation of Compound 2-3

Compound 2-3 (15.1 g, yield: 79%) was prepared in the same manner as in Step 1 of Example 2 by using Compound 2-2 (20 g, 54 mmol) and 1-bromo-3-chlorobenzene (10.3 g, 54 mmol).

Step 4) Preparation of Compound 2-4

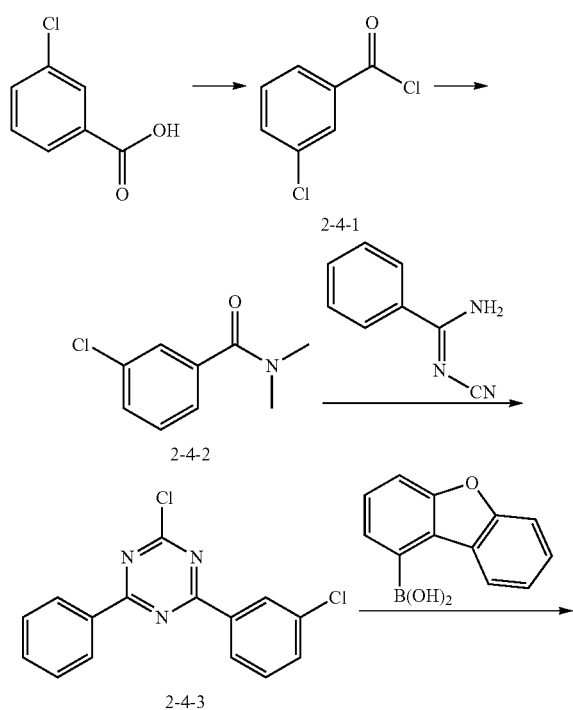

28
-continued

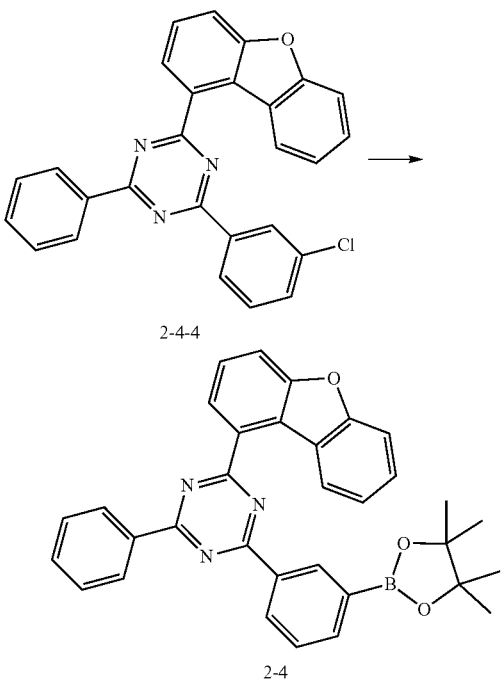

Step 4-1) Preparation of Compound 2-4-1

3-Chlorobenzoic acid (20 g, 128 mmol) was added to thionyl chloride (200 mL) and the mixture was stirred under reflux for 2 hours. After cooling to room temperature, the resulting material was distilled to produce a solid, which was washed with diethyl ether and then dried to produce Compound 2-4-1 (20.3 g, yield: 91%).

Step 4-2) Preparation of Compound 2-4-2

2.0 M solution of dimethylamine (74.8 mL, 150 mmol) and triethylamine (37.9 mL, 272 mmol) were added to 500 mL of diethyl ether, and then Compound 2-4-1 (24 g, 138 mmol) was slowly added dropwise, and then stirred for 30 minutes. The resulting solid was filtered, and then the filtrate was distilled to produce Compound 2-4-2 (19.8 g, yield: 83%).

Step 4-3) Preparation of Compound 2-4-3

N'-cyanobenzimidamide (16.8 g, 115 mmol), Compound 2-4-2 (21 g, 115 mmol) and phosphorus oxychloride (12 mL, 128 mmol) were added to 500 mL of acetonitrile and then stirred under reflux for 1 hour. After cooling to room temperature, the resulting solid was filtered, washed with water and ethanol, and then dried to produce Compound 2-4-3 (27.6 g, yield: 80%).

Step 4-4) Preparation of Compound 2-4-4

Compound 2-4-4 (21.8 g, yield: 76%) was prepared in the same manner as in Step 2 of Example 1 by using Compound 2-4-3 (20 g, 66.2 mmol) and dibenzo[b,d]furan-1-ylboronic acid (14.0 g, 66.2 mmol).

Step 4-5) Preparation of Compound 2-4

Compound 2-4 (18.4 g, yield: 76%) was prepared in the same manner as in Step 1 of Example 1 by using Compound 2-4-4 (20 g, 46 mmol).

Step 5) Preparation of Compound 2
Compound 2 (21.8 g, yield: 76%) was prepared in the same manner as in Step 5 of Example 1 by using Compound 2-3 (15 g, 42.4 mmol) and Compound 2-4 (22.3 g, 42.4 mmol).
=718
Example 3
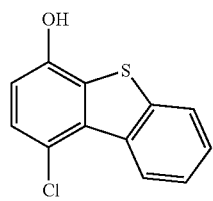
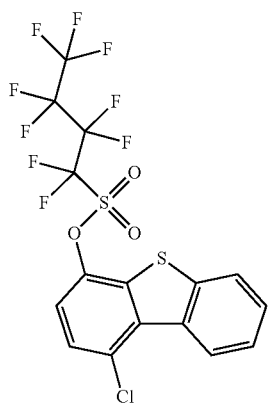
3-1
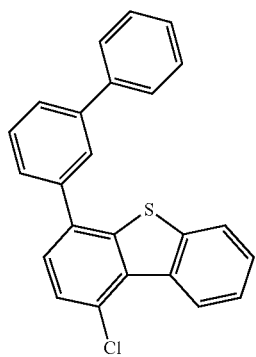
3-2
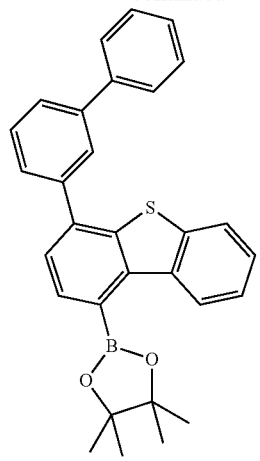
3-3
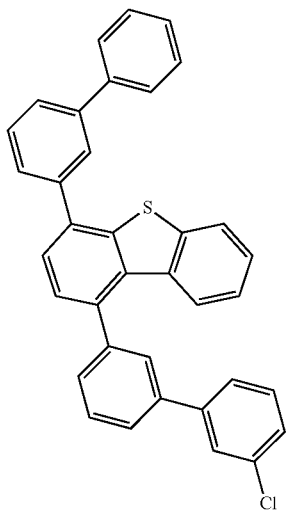
3-4
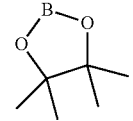
3-5

-continued

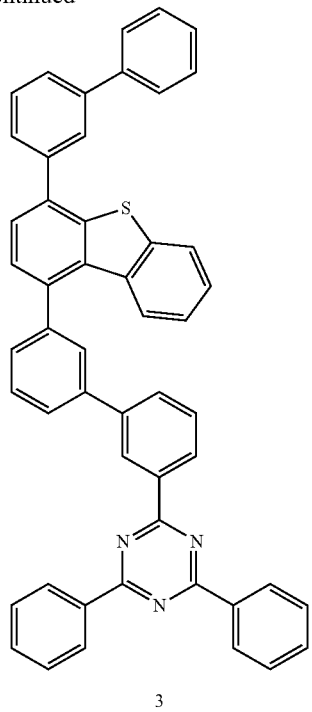

3

Step 1) Preparation of Compound 3-1

1-Chlorodibenzo[b,d]thiophen-4-ol (25 g, 95 mmol) was dispersed in 200 mL of acetonitrile, and potassium carbonate (26.3 g, 190 mmol) and 40 mL of water were added and nonafluorobutanesulfonyl fluoride (43 g, 142.5 mmol) was added thereto, and the mixture was heated to 80° C. After reaction for 6 hours, the reaction mixture was cooled to room temperature, and the solvent was removed by concentration under reduced pressure. The concentrated compound was re-dissolved in ethyl acetate and washed once with water. The organic layer was separated, treated with anhydrous magnesium sulfate, filtered, and then concentrated to produce the desired Compound 3-1 (35.8 g, yield: 73%).

Step 2) Preparation of Compound 3-2

Compound 3-2 (12.1 g, yield: 84%) was prepared in the same manner as in Step 2 of Example 1 by using Compound 3-1 (20 g, 38.7 mmol) and [1,1'-biphenyl]-3-ylboronic acid (9.2 g, 46.4 mmol).

Step 3) Preparation of Compound 3-3

Compound 3-3 (20.0 g, yield: 80%) was prepared in the same manner as in Step 1 of Example 1 by using Compound 3-2 (20 g, 54 mmol).

Step 4) Preparation of Compound 3-4

Compound 3-4 (17.4 g, yield: 77%) was prepared in the same manner as in Step 2 of Example 1 by using Compound 3-3 (20 g, 43 mmol) and 3-bromo-3'-chloro-1,1'-biphenyl (11.6 g, 43 mmol).

Step 5) Preparation of Compound 3-5

Compound 3-5 (17.9 g, yield: 76%) was prepared in the same manner as in Step 1 of Example 1 by using Compound 3-4 (20 g, 38 mmol).

Step 6) Preparation of Compound 3

Compound 3 (19.4 g, yield: 83%) was prepared in the same manner as in Step 2 of Example 1 by using Compound 3-5 (20 g, 32.5 mmol) and 2-chloro-4,6-diphenyl-1,3,5-triazine (8.7 g, 32.5 mmol).

=720

Example 4

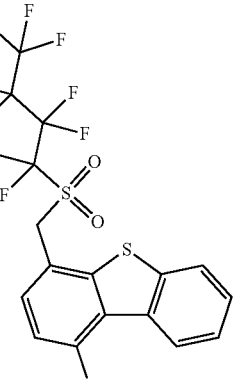

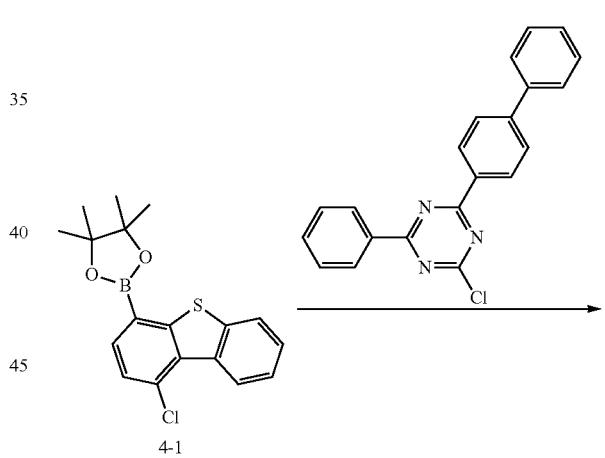

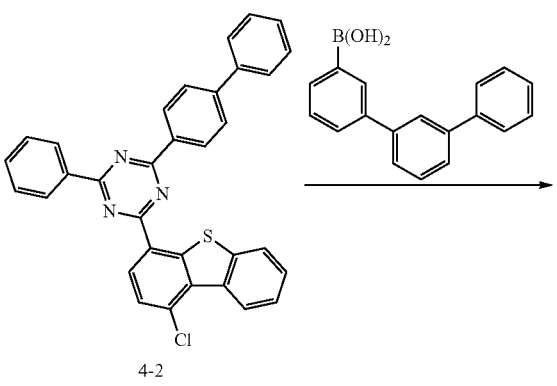

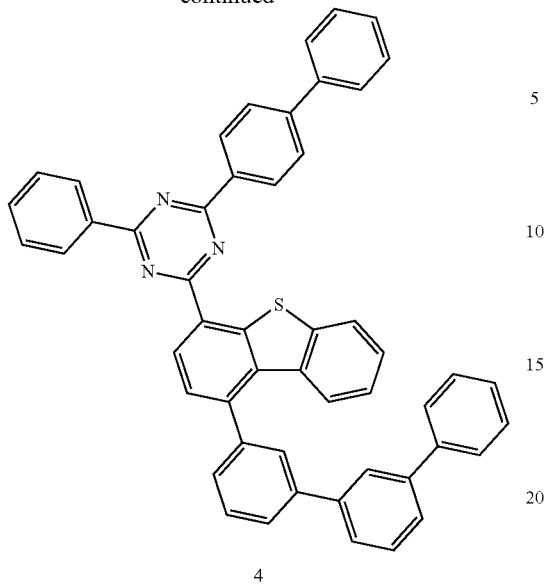

4

Step 1) Preparation of Compound 4-1

Compound 4-1 (16.6 g, yield: 83%) was prepared in the same manner as in Step 1 of Example 1 by using Compound 3-1 (30 g, 58 mmol).

Step 2) Preparation of Compound 4-2

Compound 4-2 (30.5 g, yield: 80%) was prepared in the same manner as in Step 2 of Example 1 by using Compound 4-1 (25 g, 73 mmol) and 2-(1,1'-biphenyl)-4-yl)-4-chloro-6-phenyl-1,3,5-triazine (25 g, 72.5 mmol).

Step 3) Preparation of Compound 4

Compound 4 (18.6 g, yield: 68%) was prepared in the same manner as in Step 2 of Example 1 by using Compound 4-2 (20 g, 38 mmol) and [1,1':3',1''-terphenyl]-3-ylboronic acid (10.9 g, 39.9 mmol).

=720

Example 5

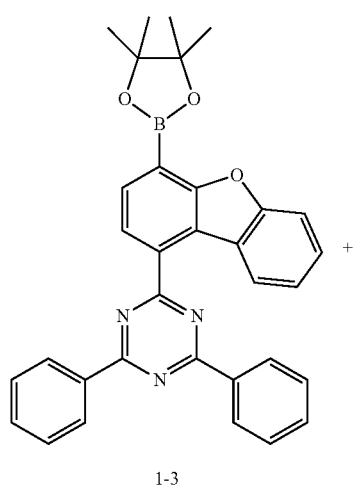

1-3

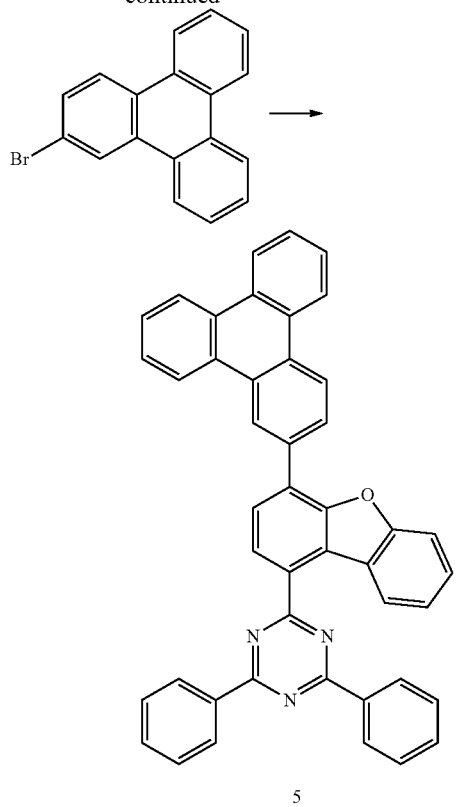

5

Compound 1-3 (20 g, 38 mmol) and 2-bromotriphenyl (11.7 g, 38 mmol) were added to 1,4-dioxane (200 mL), and potassium phosphate (14.5 g, 68 mmol) and water (50 mL) were further added thereto. Dibenzylidene acetone palladium (0.6 g, 1 mol %) and tricyclohexylphosphine (0.6 g, 1 mol %) were added under refluxing and stirring conditions, and the resulting mixture was refluxed and stirred for 12 hours. When the reaction was completed, the reaction mixture was cooled to room temperature, and the aqueous layer was separated and concentrated under reduced pressure, and the residue was then dissolved in chloroform and washed with water to separate an organic layer. The separated organic layer was dried over anhydrous magnesium sulfate and filtered. The filtrate was concentrated under reduced pressure and purified by silica column chromatography with hexane and chloroform to produce Compound 5 (15.9 g, yield: 67%).

=626

Example 6

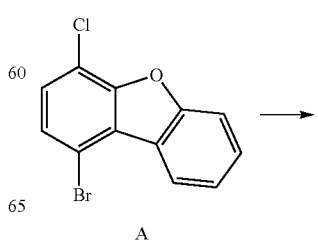

A

-continued

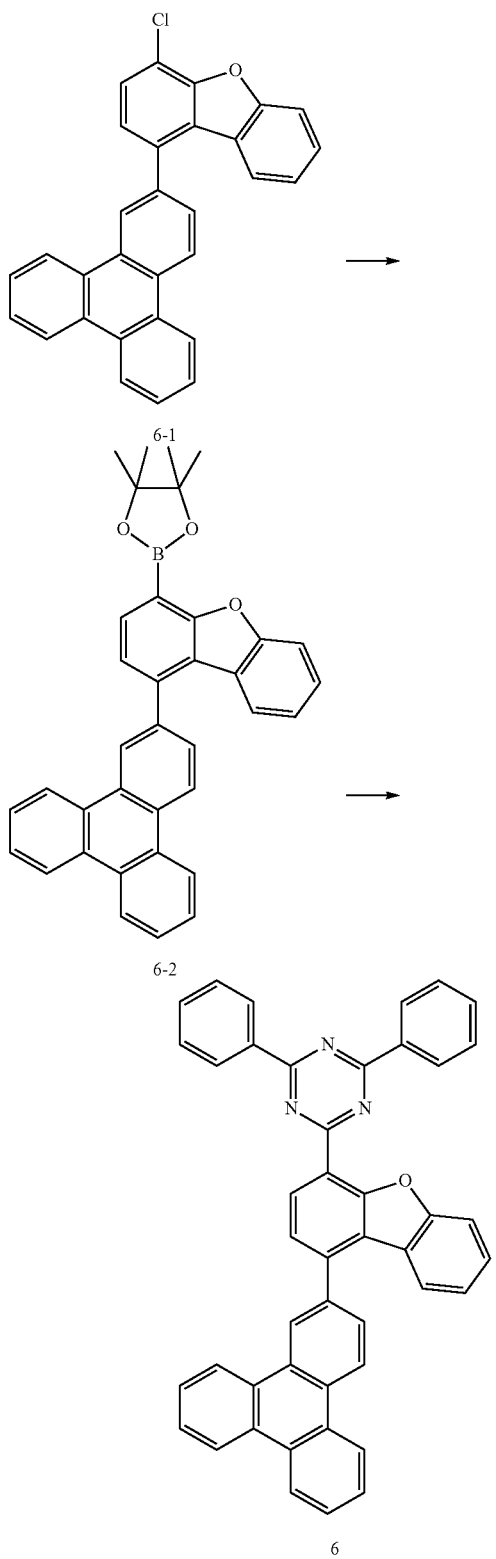

Compound 6-1 (30.4 g, yield: 80%) was prepared in the same manner as in Preparation of Compound 2-1 by using Compound A (25 g, 88.8 mmol) and triphenylene-2-ylboronic acid (22.2 g, 88.8 mmol).

Compound 6-2 (28.4 g, yield: 77%) was prepared in the same manner as in Preparation of Compound 2-2 by using Compound 6-1 (30.4 g, 71.0 mmol).

Compound 6 (23.3 g, yield: 68%) was prepared in the same manner as in Preparation of Compound 3 by using Compound 6-2 (28.4 g, 54.7 mmol) and 2-chloro-4,6-diphenyl-1,3,5-triazine (14.6 g, 54.7 mmol).

=626

Experimental Example 1

A glass substrate on which ITO (indium tin oxide) was coated as a thin film to a thickness of 1,300 Å was put into distilled water in which a detergent was dissolved, and ultrasonically cleaned. In this case, a product manufactured by Fischer Co., was used as the detergent, and as the distilled water, distilled water filtered twice using a filter manufactured by Millipore Co., was used. After the ITO was cleaned for 30 minutes, ultrasonic cleaning was repeated twice using distilled water for 10 minutes. After the cleaning with distilled water was completed, the substrate was ultrasonically cleaned with solvents of isopropyl alcohol, acetone, and methanol, then dried, and then transferred to a plasma cleaner. In addition, the substrate was cleaned for 5 minutes using oxygen plasma, and then transferred to a vacuum depositor.

On the transparent ITO electrode prepared as above, a compound of the following formula HI-1 was thermally vacuum-deposited to a thickness of 50 Å to form a hole injection layer. A compound of the following formula HT-1 was thermally vacuum-deposited on the hole injection layer in a thickness of 250 Å to form a hole transfer layer, and a compound of the following formula HT-2 was vacuum deposited on the hole transport layer in a thickness of 50 Å to form an electron blocking layer. Then, the compound of Example 1 previously prepared and a compound of the following formula GD were deposited on the electron blocking layer in a thickness of 300 Å by co-evaporation at a weight ratio shown in Table 1 below to form a light emitting layer. A compound of the following formula ET-1 was vacuum deposited on the light emitting layer in a thickness of 250 Å to form an electron transport layer. A compound of the following formula ET-2 was co-deposited with 2 wt % Li on the electron transport layer to form an electron injection layer with a thickness of 100 Å. Aluminum was deposited on the electron injection layer in a thickness of 1000 Å to form a cathode.

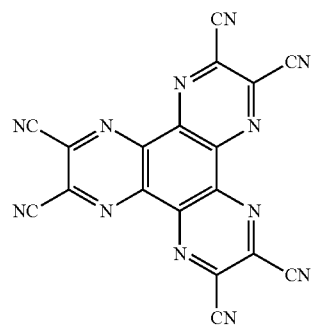

HI-1

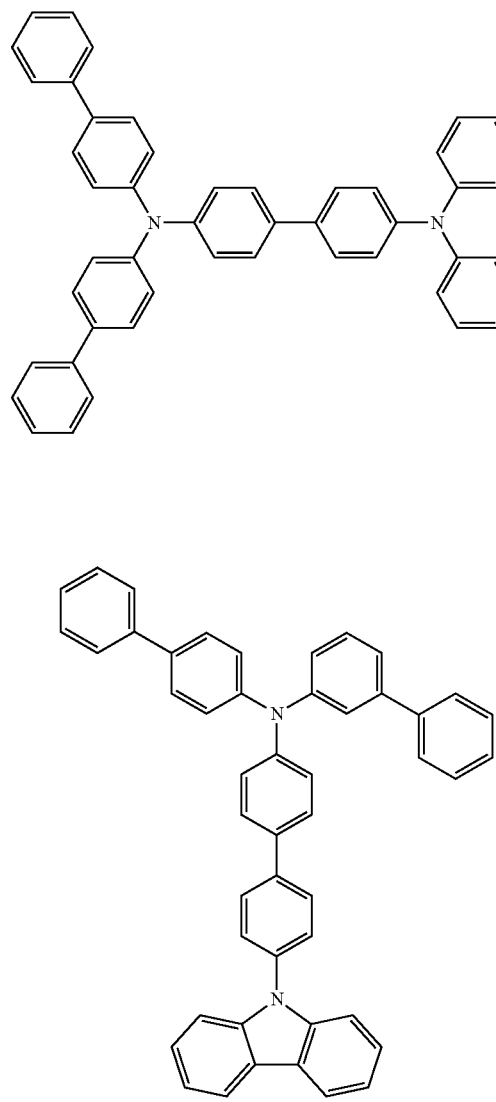
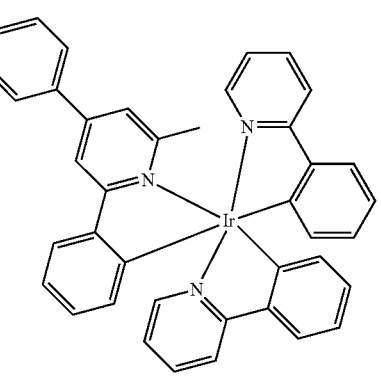
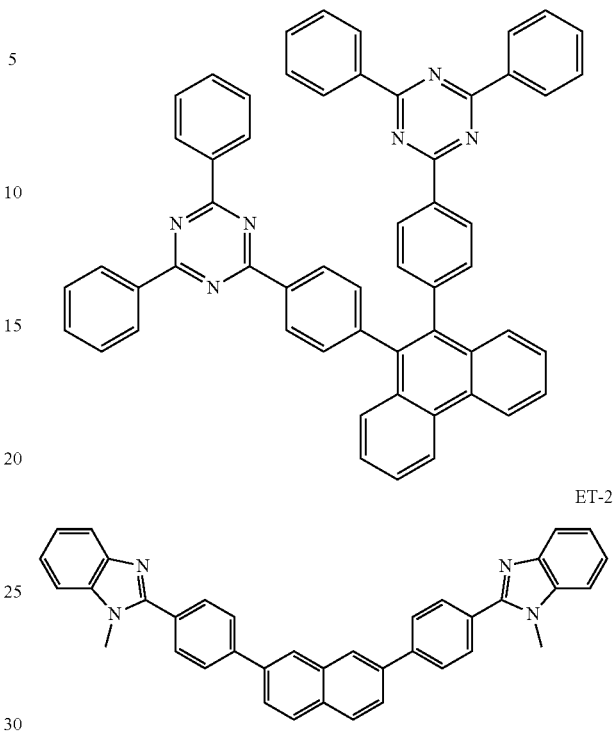

In the above-mentioned process, the vapor deposition rate of the organic material was maintained at 0.4 to 07 Å/sec, the vapor deposition rate of aluminum was maintained at 2 Å/sec, and the degree of vacuum during vapor deposition was maintained at 1× to 5×10 torr.

Experimental Examples 2 to 8

The organic light emitting devices of Examples 2 to 8 were respectively manufactured in the same manner as in Example 1, except that the materials and contents used during formation of the light emitting layers were changed as shown in Table 1 below. On the other hand, Compound GH-2 used in Experimental Examples 5 to 8 is as follows:

Comparative Experimental Examples 1 to 6

The organic light emitting devices of Comparative Examples 1 to 6 were respectively manufactured in the same manner as in Example 1, except that the contents of the phosphorescent host material and the dopant used during formation of the light emitting layers were changed as shown in Table 1 below. In this case, the host materials B to F are as follows.

compound B

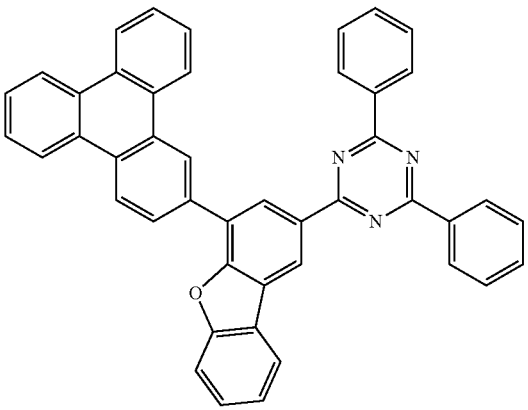

compound C

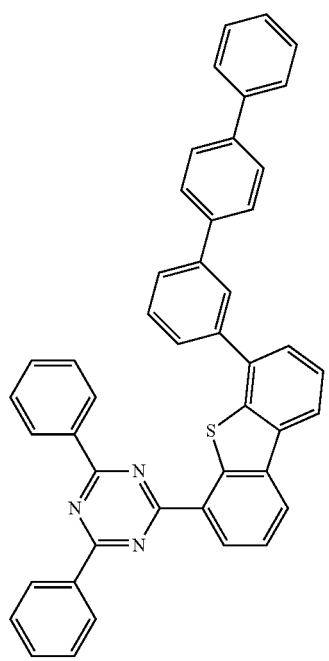

compound D

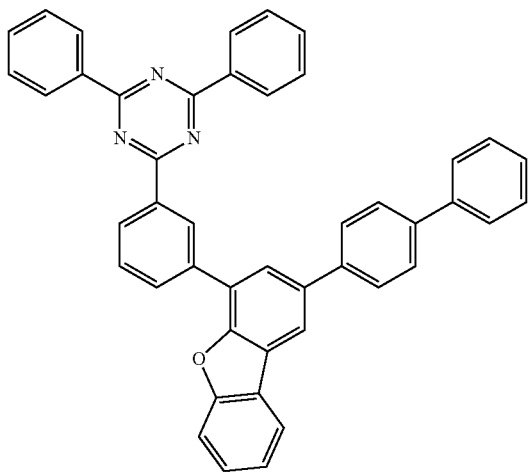

compound E

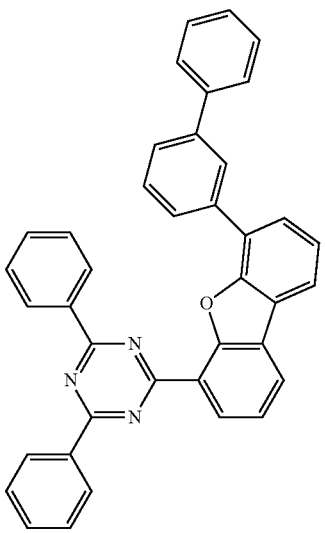

compound F

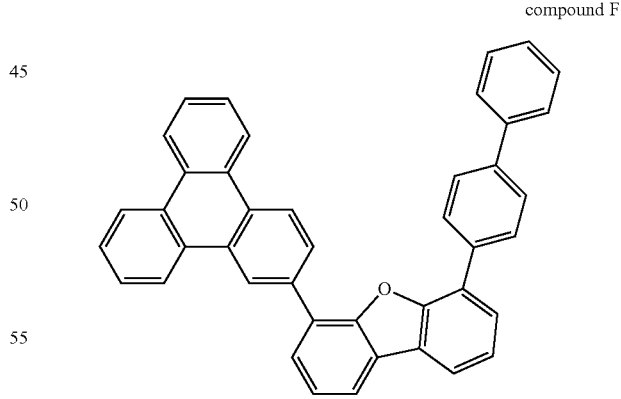

The voltage, efficiency, color coordinate, and lifetime were measured by applying a current to the organic light emitting devices manufactured in the Experimental Examples and Comparative Experimental Examples, and the results are shown in Table 1 below. At this time, T95 means the time required for the luminance to be reduced to 95% when the initial luminance at the current density of 20 mA/cm is taken as 100%.

TABLE 1

| | Compound (weight ratio) | Voltage (V) (@10) | Efficiency (Cd/A) (@10) | Color coordinate (x, y) | Lifetime (T95, hr) (@20 mA/cm |
|---|---|---|---|---|---|
| Experimental Example 1 | Compound 1:GD (93:7) | 3.03 | 64.1 | (0.313, 0.634) | 32.6 |
| Experimental Example 2 | Compound 2:GD (87:13) | 3.12 | 66.0 | (0.326, 0.628) | 28.6 |
| Experimental Example 3 | Compound 3:GD (93:7) | 3.10 | 68.6 | (0.319, 0.631) | 32.6 |
| Experimental Example 4 | Compound 4:GD (90:10) | 3.02 | 62.3 | (0.323, 0.629) | 38.2 |
| Experimental Example 5 | Compound 1:GH-2:GD (45:45:10) | 3.16 | 64.9 | (0.324, 0.629) | 63.1 |
| Experimental Example 6 | Compound 4:GH-2:GD (45:45:10) | 3.11 | 65.7 | (0.323, 0.629) | 67.6 |
| Experimental Example 7 | Compound 5:GH-2:GD (45:45:10) | 3.20 | 64.2 | (0.324, 0.629) | 70.2 |
| Experimental Example 8 | Compound 6:GH-2:GD (45:45:10) | 3.21 | 66.1 | (0.324, 0.630) | 65.2 |
| Comparative Experimental Example 1 | Compound B:GD (93:7) | 3.28 | 56.8 | (0.316, 0.633) | 15.2 |
| Comparative Experimental Example 2 | Compound C:GD (90:10) | 3.31 | 61.5 | (0.321, 0.631) | 18.2 |
| Comparative Experimental Example 3 | Compound B:GH-2:GD (45:45:10) | 3.41 | 55.9 | (0.325, 0.629) | 30.1 |
| Comparative Experimental Example 4 | Compound D:GH-2:GD (45:45:10) | 3.23 | 60.2 | (0.324, 0.629) | 25.2 |
| Comparative Experimental Example 5 | Compound E:GH-2:GD | 3.33 | 62.1 | (0.323, 0.629) | 35.6 |
| Comparative Experimental Example 6 | Compound F:GD (90:10) | 5.21 | 30.1 | (0.324, 0.629) | 5.2 |

As shown in Table 1, it could be confirmed that the driving voltage, efficiency and lifetime of the organic light emitting devices using the compounds according to the present disclosure were remarkably improved as compared with those of the organic light emitting device using the compounds of Comparative Explanation of Item Numbers

| | |
|---|---|
| 1: substrate | 2: anode |
| 3: light emitting layer | 4: cathode |
| 5: hole injection layer | 6: hole transport layer |
| 7: light emitting layer | 8: electron transport layer |

The invention claimed is:

1. A compound e following Chemical Formula 2:

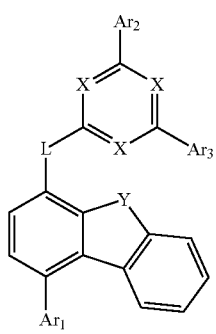

[Chemical Formula 2]

wherein in Chemical Formula 2:
each X is N;
Y is O or S;

L is a bond, a substituted or unsubstituted C$_{6-60}$ arylene, or a substituted or unsubstituted C$_{2-60}$ heteroarylene containing at least one hetero atom selected from the group consisting of N, O and S;

Ar$_1$ is

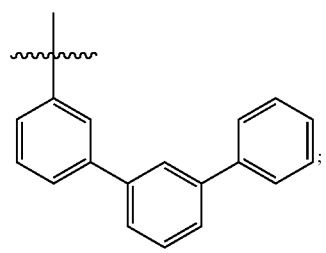 [SMILES: *c1cccc(-c2cccc(-c3ccccc3)c2)c1]

and

Ar$_2$ and Ar$_3$ are each independently a substituted or unsubstituted C$_{6-60}$ aryl or a substituted or unsubstituted C$_{2-60}$ heteroaryl containing at least one hetero atom selected from the group consisting of N, O and S.

2. The compound of claim 1, wherein:

L is a bond, phenylene, biphenyldiyl, or terphenyldiyl.

3. The compound of claim 1, wherein:

Ar$_2$ and Ar$_3$ are each independently phenyl, biphenylyl, dibenzofuranyl, or dibenzothiophenyl.

4. The compound of claim 1, wherein:

Ar$_2$ is phenyl; and

Ar$_3$ is phenyl, biphenylyl, dibenzofuranyl, or dibenzothiophenyl.

5. The compound of claim 1, wherein:

the compound of Chemical Formula 2 is any one selected from the group consisting of the following compounds:

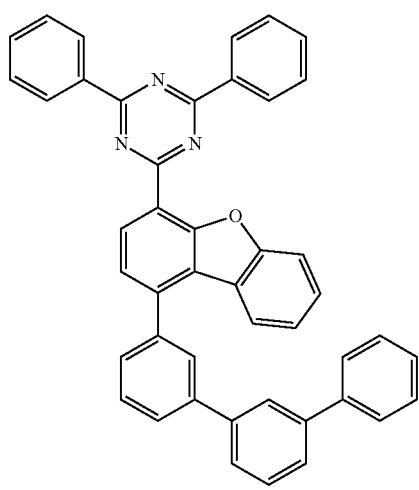

-continued

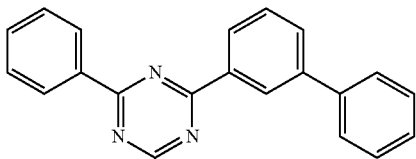

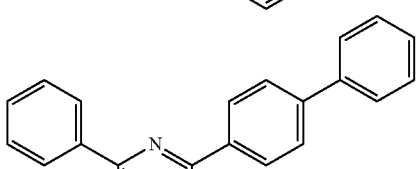

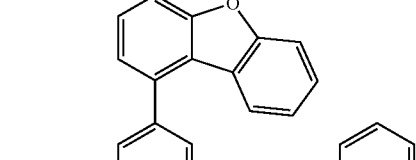

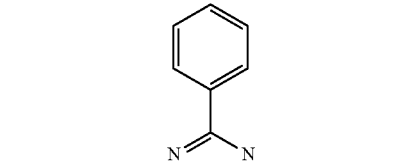

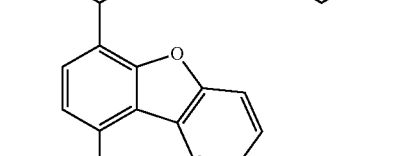

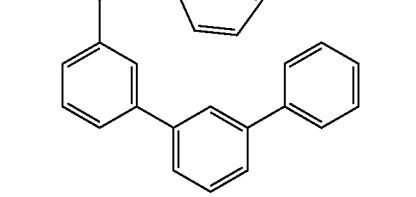

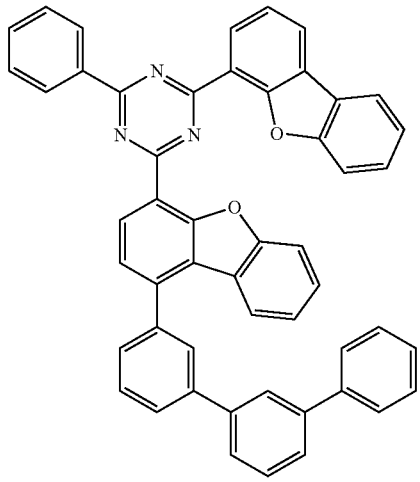

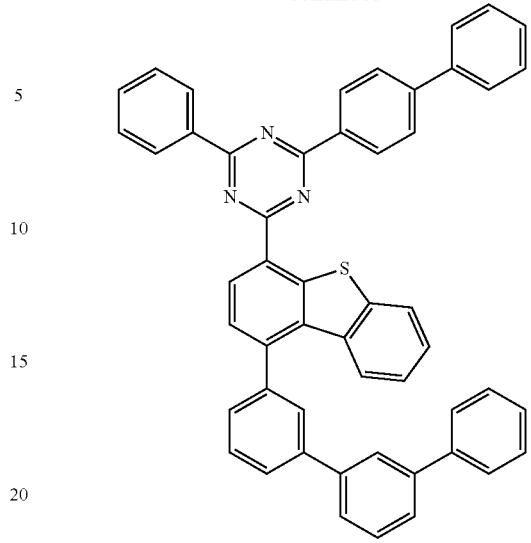

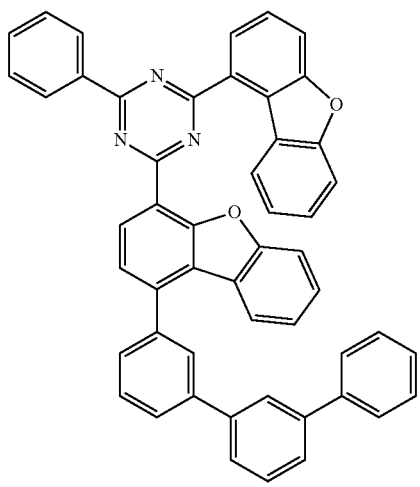

6. An organic light emitting device, comprising a first electrode; a second electrode provided opposite to the first electrode; and one or more organic material layers provided between the first electrode and the second electrode, wherein one or more one layers of the organic material layers comprise the compound according to claim 1.

7. The organic light emitting device of claim 6, wherein the one or more organic layers comprises a hole injection layer, a hole transport layer, a light emitting layer, an electron transport layer, an electron injection layer or a combination thereof.

8. The organic light emitting device of claim 6, wherein the one or more organic layers comprises a hole injection layer, a hole transport layer, or a layer simultaneously performing hole injection and transport, and the hole injection layer, the hole transport layer, and the layer simultaneously performing hole injection and transport include the compound of Chemical Formula 2.

9. The organic light emitting device of claim 6, wherein the one or more organic layers comprises a light emitting layer, and the light emitting layer includes the compound of Chemical Formula 2.

10. The organic light emitting device of claim 6, wherein the one or more organic layers comprises an electron transport layer or an electron injection layer, and the electron transport layer or the electron injection layer includes the compound of Chemical Formula 2.

11. The organic light emitting device of claim 6, wherein the one or more organic layers comprises a light emitting layer and an electron transport layer, and the electron transport layer includes the compound of Chemical Formula 2.

* * * * *